US006569125B2

(12) United States Patent
Jepson et al.

(10) Patent No.: US 6,569,125 B2
(45) Date of Patent: May 27, 2003

(54) PRE-SLIT INJECTION SITE AND TAPERED CANNULA

(75) Inventors: Steven C. Jepson, Palatine, IL (US); Thomas E. Dudar, Palatine, IL (US); Michael J. Finley, Park City, IL (US); Vincent C. Desecki, Ingleside, IL (US)

(73) Assignee: Baxter International Inc, Deerfield, IL (US)

( * ) Notice: Subject to any disclaimer, the term of this patent is extended or adjusted under 35 U.S.C. 154(b) by 0 days.

(21) Appl. No.: 09/907,234

(22) Filed: Jul. 17, 2001

(65) Prior Publication Data

US 2001/0047154 A1 Nov. 29, 2001

Related U.S. Application Data

(63) Continuation of application No. 09/181,975, filed on Oct. 29, 1998, now Pat. No. 6,261,266, which is a continuation of application No. 08/695,040, filed on Aug. 9, 1996, now Pat. No. 5,899,888, which is a continuation of application No. 07/325,617, filed on Mar. 17, 1989, now abandoned, which is a continuation-in-part of application No. 07/217,004, filed on Jul. 8, 1988, now abandoned, which is a continuation-in-part of application No. 07/147,414, filed on Jan. 25, 1988, now abandoned.

(51) Int. Cl.[7] ............................................. A61M 5/28
(52) U.S. Cl. ..................................... 604/201; 604/905
(58) Field of Search ............................... 604/189, 523, 604/533–539, 905, 164, 174, 256; 137/223

(56) References Cited

U.S. PATENT DOCUMENTS

| | | | |
|---|---|---|---|
| 1,180,665 A | 4/1916 | McElroy | |
| 2,102,704 A | 12/1937 | Hein | |
| 2,183,900 A | 12/1939 | Voit et al. | |
| 2,325,929 A | 8/1943 | Amesbury et al. | |
| 2,436,291 A | 12/1948 | Daniel | |

(List continued on next page.)

FOREIGN PATENT DOCUMENTS

| | | |
|---|---|---|
| AU | 13945 | 10/1971 |
| CA | 964544 | 3/1975 |
| CA | 1043744 | 12/1978 |
| CA | 1215945 | 12/1986 |
| CH | 361364 | 5/1962 |
| DD | 35387 | 11/1965 |
| DE | 0855319 | 11/1952 |
| DE | 7443346 | 10/1977 |
| DE | 441387 | 11/1978 |

(List continued on next page.)

OTHER PUBLICATIONS

Industrie BORLA S.p.A. General Catalog, 1980 p. 1, PF0084.
Industrie BORLA S.p.A. Catalogs, Each of 1981–1992 (Any of PF0084, PF0091, PF0358, PF0241, PF0392, PF0218).
Components for IV. infusion and blood transfusion sets (patient–side terminals) Undated (1980–1986); pp. PF0358, PF0241, PF0392, PF0218.
Travenol Nutrition Products, 1982 pp. BX 77331, 77533–BX 77534.
Schematic Drawing of Automix (Undated), pp. BX 77314.

(List continued on next page.)

*Primary Examiner*—Manuel Mendez
(74) *Attorney, Agent, or Firm*—Jeffrey C. Nichols; Mark J. Buonaiuto; Francis C. Kowalik

(57) ABSTRACT

A pre-slit injection site (34) includes a housing (40) with a flow path therethrough. A first end (42) of the housing (40) carries a pre-slit septum (52). One form of a blunt cannula (98), usable with the injection site (34), carries a locking member (100). When the pre-slit injection site (34) slidably receives the blunt cannula (98), the locking member (100) latches to the injection site (34) and creates a mechanically coupled unit. Another form of the cannula (280) includes a tube having a tapered distal end region (298) and having elongate discharge slots (294) for reducing contact surface area and for directing the flow laterally out of the cannula. The cannula may also include a rounded lead post (330), an annular barb (394), and axially oriented grooves (268).

24 Claims, 16 Drawing Sheets

U.S. PATENT DOCUMENTS

| | | |
|---|---|---|
| 2,546,672 A | 3/1951 | LeClair |
| 2,577,780 A | 12/1951 | Lockhart |
| 2,579,724 A | 12/1951 | Breakstone |
| 2,579,725 A | 12/1951 | Breakstone |
| 2,908,274 A | 10/1959 | Bujan |
| 2,912,980 A | 11/1959 | Beachum et al. |
| 2,989,053 A | 6/1961 | Hamilton |
| 2,998,635 A | 9/1961 | Burritt, Jr. et al. |
| 3,055,363 A | 9/1962 | Eckhart |
| 3,057,350 A | 10/1962 | Cowley |
| 3,064,652 A | 11/1962 | Corcoran et al. |
| 3,233,727 A | 2/1966 | Wilson |
| 3,245,698 A | 4/1966 | Fromknecht |
| 3,313,299 A | 4/1967 | Spademan |
| 3,332,418 A | 7/1967 | Brody |
| 3,376,866 A | 4/1968 | Ogle |
| 3,394,954 A | 7/1968 | Sams |
| 3,447,570 A | 6/1969 | Collins |
| 3,478,743 A | 11/1969 | Ericson |
| 3,577,992 A | 5/1971 | Merry et al. |
| 3,593,909 A | 7/1971 | Bergmann |
| 3,598,124 A | 8/1971 | Andersen |
| 3,602,009 A | 8/1971 | Powell |
| 3,604,420 A | 9/1971 | Vaillancourt |
| 3,695,478 A | 10/1972 | Sic et al. |
| 3,729,031 A | 4/1973 | Baldwin |
| 3,729,032 A | 4/1973 | Tischlinger |
| 3,741,217 A | 6/1973 | Ciarico |
| 3,746,001 A | 7/1973 | Ralston, Jr. |
| 3,768,473 A | 10/1973 | Shields |
| 3,770,155 A | 11/1973 | Novitch |
| 3,776,229 A | 12/1973 | McPhee |
| 3,823,840 A | 7/1974 | Zackheim |
| 3,837,381 A | 9/1974 | Arroyo |
| 3,848,593 A | 11/1974 | Baldwin |
| 3,851,647 A | 12/1974 | Monestere, Jr. et al. |
| 3,853,127 A | 12/1974 | Spademan |
| 3,900,028 A | 8/1975 | McPhere |
| 3,904,059 A | 9/1975 | Belolamy, Jr. et al. |
| 3,976,073 A | 8/1976 | Quick et al. |
| 3,977,400 A | 8/1976 | Moorehead |
| 3,986,508 A | 10/1976 | Barrington |
| 3,990,445 A | 11/1976 | Lundquist |
| 3,994,293 A | 11/1976 | Ferro |
| 3,995,630 A | 12/1976 | Van de Veerdonk |
| 4,000,739 A | 1/1977 | Stevens |
| 4,000,740 A | 1/1977 | Mittleman |
| 4,048,995 A | 9/1977 | Mittleman |
| 4,048,996 A | 9/1977 | Mittleman |
| 4,066,556 A | 1/1978 | Vaillancourt |
| 4,076,285 A | 2/1978 | Martinez |
| 4,123,081 A | 10/1978 | Ellinger |
| 4,123,091 A | 10/1978 | Cosentino et al. |
| 4,127,131 A | 11/1978 | Vaillancourt |
| 4,130,932 A | 12/1978 | Epmeier |
| 4,133,441 A | 1/1979 | Mittleman |
| 4,134,512 A | 1/1979 | Nugent |
| 4,143,853 A | 3/1979 | Abramson |
| 4,177,814 A | 12/1979 | Knepshield et al. |
| 4,192,919 A | 3/1980 | Raghavachari |
| 4,197,848 A | 4/1980 | Garrett et al. |
| 4,205,675 A | 6/1980 | Vaillancourt |
| 4,219,912 A | 9/1980 | Adams |
| 4,232,669 A | 11/1980 | Nitshke |
| 4,236,880 A | 12/1980 | Archibald |
| 4,243,034 A | 1/1981 | Brandt |
| 4,243,150 A | 1/1981 | Gunne |
| 4,246,899 A | 1/1981 | Loseff |
| 4,259,276 A | 3/1981 | Rawlings |
| 4,276,170 A | 6/1981 | Vaillancourt |
| 4,277,226 A | 7/1981 | Archibald |
| 4,289,129 A | 9/1981 | Turner |
| 4,294,249 A | 10/1981 | Sheehan et al. |
| 4,296,949 A | 10/1981 | Muetterties et al. |
| 4,303,067 A | 12/1981 | Connolly et al. |
| 4,311,137 A | 1/1982 | Gerard |
| 4,322,201 A | 3/1982 | Archibald |
| 4,326,569 A | 4/1982 | Vaillancourt |
| 4,331,254 A | 5/1982 | Haggerty |
| 4,334,551 A | 6/1982 | Pfister |
| 4,346,703 A | 8/1982 | Dennehey et al. |
| 4,360,024 A | 11/1982 | Wallace |
| 4,362,156 A | 12/1982 | Feller et al. |
| 4,372,100 A | 2/1983 | Miller et al. |
| 4,387,879 A | 6/1983 | Tauschinski |
| 4,405,316 A | 9/1983 | Mittelman |
| 4,405,320 A | 9/1983 | Cracauer et al. |
| 4,411,661 A | 10/1983 | Kersten |
| 4,411,662 A | 10/1983 | Pearson |
| 4,412,573 A | 11/1983 | Zdeb |
| 4,416,661 A | 11/1983 | Norman et al. |
| 4,417,888 A | 11/1983 | Consentino et al. |
| 4,424,833 A | 1/1984 | Spector et al. |
| 4,430,081 A | 2/1984 | Timmermans |
| 4,434,822 A | 3/1984 | Bellamy et al. |
| 4,436,519 A | 3/1984 | O'Neill |
| 4,439,188 A | 3/1984 | Dennehey et al. |
| 4,445,896 A | 5/1984 | Gianturco |
| 4,475,548 A | 10/1984 | Muto |
| 4,496,348 A | 1/1985 | Genese et al. |
| 4,511,359 A | 4/1985 | Vaillancourt |
| 4,535,820 A | 8/1985 | Raines |
| 4,545,367 A | 10/1985 | Tucci |
| 4,559,043 A | 12/1985 | Whitehouse et al. |
| 4,578,063 A | 3/1986 | Inman et al. |
| 4,588,403 A | 5/1986 | Weiss et al. |
| 4,589,879 A | 5/1986 | Pearson |
| 4,601,703 A | 7/1986 | Herlitze |
| 4,607,671 A | 8/1986 | Aalto et al. |
| 4,607,868 A | 8/1986 | Harvey et al. |
| 4,610,374 A | 9/1986 | Buehler |
| 4,610,469 A | 9/1986 | Wolff-Mooij |
| 4,610,665 A | 9/1986 | Matsumoto et al. |
| 4,610,674 A | 9/1986 | Suzuki et al. |
| 4,617,012 A | 10/1986 | Vaillancourt |
| 4,624,393 A | 11/1986 | Lopez |
| 4,626,245 A | 12/1986 | Weinstein |
| 4,634,424 A | 1/1987 | O'Boyle |
| 4,637,817 A | 1/1987 | Archibald et al. |
| 4,638,809 A | 1/1987 | Kuperus |
| 4,645,495 A | 2/1987 | Vaillancourt |
| 4,650,475 A | 3/1987 | Smith et al. |
| 4,653,010 A | 3/1987 | Figler et al. |
| 4,655,750 A | 4/1987 | Vaillancourt |
| 4,655,752 A | 4/1987 | Honkanen et al. |
| 4,662,878 A | 5/1987 | Lindmayer |
| 4,673,386 A | 6/1987 | Gordon |
| 4,673,390 A | 6/1987 | Archibald |
| 4,673,393 A | 6/1987 | Suzuki et al. |
| 4,675,020 A | 6/1987 | McPhee |
| 4,683,916 A | 8/1987 | Raines |
| 4,704,177 A | 11/1987 | Vaillancourt |
| 4,705,506 A | 11/1987 | Archibald |
| 4,711,636 A | 12/1987 | Bierman |
| 4,714,463 A | 12/1987 | Archibald |
| 4,718,467 A | 1/1988 | DiGianfilippo et al. |
| 4,723,550 A | 2/1988 | Bales et al. |
| 4,735,311 A | 4/1988 | Lowe et al. |
| 4,745,950 A | 5/1988 | Mathieu |
| 4,752,292 A | 6/1988 | Lopez et al. |
| 4,758,225 A | 7/1988 | Cox et al. |

| | | | | | |
|---|---|---|---|---|---|
| 4,759,756 A | 7/1988 | Forman et al. | 5,199,947 A | 4/1993 | Lopez et al. |
| 4,760,847 A | 8/1988 | Vaillancourt | 5,211,638 A | 5/1993 | Dudar et al. |
| 4,763,648 A | 8/1988 | Wyatt | 5,344,414 A | 9/1994 | Lopez et al. |
| 4,765,588 A | 8/1988 | Atkinson | 5,447,495 A | 9/1995 | Lynn et al. |
| 4,766,843 A | 8/1988 | Murakami et al. | 6,261,266 B1 * | 7/2001 | Jepson et al. ............ 604/201 |
| 4,768,568 A | 9/1988 | Fournier et al. | | | |
| 4,770,295 A | 9/1988 | Carveth et al. | | | |

FOREIGN PATENT DOCUMENTS

| | | |
|---|---|---|
| 4,776,843 A | 10/1988 Martinez et al. | |
| 4,781,680 A | 11/1988 Redmond et al. | DE 3303718 10/1984 |
| 4,786,281 A | 11/1988 Valentini et al. | DE 8425197 10/1985 |
| 4,789,014 A | 12/1988 DiGianfilippo et al. | DE 3627978 8/1986 |
| 4,796,615 A | 1/1989 Bullock et al. | EP 0021405 1/1981 |
| 4,798,594 A | 1/1989 Hillstead | EP 0050459 4/1982 |
| 4,804,366 A | 2/1989 Zdeb et al. | EP 86308132 1/1984 |
| 4,809,679 A | 3/1989 Shimonaka et al. | EP 0109903 5/1984 |
| 4,810,241 A | 3/1989 Rogers | EP 0111723 6/1984 |
| 4,813,937 A | 3/1989 Vaillancourt | EP 0114677 8/1984 |
| 4,822,343 A | 4/1989 Biser | EP 0116986 8/1984 |
| 4,823,833 A | 4/1989 Hogan et al. | EP 0157224 10/1985 |
| 4,826,491 A | 5/1989 Schramm | EP 0169704 1/1986 |
| 4,834,152 A | 5/1989 Howson et al. | EP 0220911 5/1987 |
| 4,834,709 A | 5/1989 Banning et al. | EP 0232074 8/1987 |
| 4,834,716 A | 5/1989 Oge, III | EP 0143517 5/1989 |
| 4,838,855 A | 6/1989 Lynn | EP 0319764 6/1989 |
| 4,840,017 A | 6/1989 Miller et al. | EP 0324839 8/1989 |
| 4,842,587 A | 6/1989 Poncy | EP 0344907 12/1989 |
| 4,842,591 A | 6/1989 Luther | EP 0367549 5/1990 |
| 4,850,978 A | 7/1989 Dudar et al. | EP 0413386 2/1991 |
| 4,857,062 A | 8/1989 Russell | EP 0471335 2/1992 |
| 4,874,369 A | 10/1989 Kulle et al. | EP 0485028 5/1992 |
| 4,874,377 A | 10/1989 Newgard et al. | EP 0495330 7/1992 |
| 4,874,378 A | 10/1989 Hillstead | EP 0563617 10/1993 |
| 4,878,516 A | 11/1989 Mathieu | FR 1171578 1/1959 |
| 4,886,495 A | 12/1989 Reynolds | FR 1373027 4/1964 |
| 4,889,256 A | 12/1989 Fowies | FR 2439022 6/1980 |
| 4,892,222 A | 1/1990 Schmidt et al. | FR 2539303 7/1984 |
| 4,895,346 A | 1/1990 Steigerwald | GB 893754 4/1962 |
| 4,895,565 A | 1/1990 Hiilstead | GB 1078650 8/1967 |
| 4,909,794 A | 3/1990 Haber et al. | GB 2033230 5/1980 |
| 4,909,798 A | 3/1990 Fleischhacker et al. | GB 2067075 11/1983 |
| 4,911,705 A | 3/1990 Heinzerling et al. | GB 2143134 2/1985 |
| 4,915,687 A | 4/1990 Sivert | IT 548632 9/1956 |
| 4,915,690 A | 4/1990 Cone et al. | JP 50-9195 3/1975 |
| 4,932,633 A | 6/1990 Johnson et al. | JP 55-1628 1/1980 |
| 4,932,944 A | 6/1990 Jagger et al. | JP 56-501668 11/1981 |
| 4,935,010 A | 6/1990 Cox et al. | JP 62-43697 9/1987 |
| 4,936,832 A | 6/1990 Vaillancourt | JP 3-504571 10/1991 |
| 4,946,445 A | 8/1990 Lynn | JP 1898158 1/1995 |
| 4,950,260 A | 8/1990 Bonaldo | SU 1625650 2/1991 |
| 4,961,729 A | 10/1990 Vaillancourt | WO WO 81/01654 6/1981 |
| 4,966,586 A | 10/1990 Vaillancourt | WO WO 85/01513 2/1985 |
| 4,967,811 A | 11/1990 DiGianfilippo et al. | WO WO 89/06553 7/1989 |
| 4,981,469 A | 1/1991 Whitehouse et al. | WO WO 90/12606 1/1990 |
| 4,994,029 A | 2/1991 Rohrbough | WO WO 90/11103 10/1990 |
| 4,998,713 A | 3/1991 Vaillancourt | WO WO 91/05581 5/1991 |
| 5,009,391 A | 4/1991 Steigerwald | WO WO 91/07206 5/1991 |
| 5,009,640 A | 4/1991 Pyret et al. | WO WO 91/10459 7/1991 |
| 5,017,192 A | 5/1991 Dodge et al. | WO WO 92/04936 4/1992 |
| 5,053,014 A | 10/1991 Van Heugten | |
| 5,059,172 A | 10/1991 Sutherland et al. | OTHER PUBLICATIONS |
| 5,059,186 A | 10/1991 Yamamoto et al. | |
| 5,071,404 A | 12/1991 Larkin et al. | Section 5—Operation (Undated), pp. 5–2 through 5–14 BX77315–77328. |
| 5,071,413 A | 12/1991 Utterberg | |
| 5,078,689 A | 1/1992 Keller | Travenol CYSTOFLOT advertising literature (Undated) pp. BX 77333–77334. |
| 5,080,654 A | 1/1992 Picha et al. | |
| 5,088,995 A | 2/1992 Packard et al. | Compounding Perspectives: A Newsletter for Users of AUTOMIX® & AUTOMIX® PLUS Compounders Fall 1986 pp. BX 77297–BX77300. |
| 5,100,394 A | 3/1992 Dudar et al. | |
| 5,135,489 A | 8/1992 Jepson et al. | |
| 5,149,327 A | 9/1992 Oshiyama | |
| 5,178,607 A | 1/1993 Lynn et al. | Clintec Nutrition Travesorb® Dual Port Feeding Tubes, (Undated) pp. BX 77536–BX77539. |
| 5,188,620 A | 2/1993 Jepson et al. | |

Travenol Laboratories Parenteral Products Division Catalog, 1982—Photograph.

"IV. Sets and Solutions Safeline No–Needle IV. System", article by Kendall McGaw Laboratories, Inc. (Undated).

1991 Annual Report of Becton Dickinson, 1991.

"Needlestick–Prevention Devices", Special Report and Product Review, Health Devices, May 1991, vol. 20, No. 5, pp. 154–181.

IMED Needleless System, 1993.

Ped–Pod Oral Dispenser and Hy–Pod Hypodermic Syringes, SoloPack Laboratories, Elk Grove Village, IL (Undated).

European Application 84 100 561.4, to Lopez, Jan. 19, 1984 (filing date), 1–4 and Declaration of Dr. Lopez.

Declaration of Dr. George A. Lopez, United States patent application No. 06/606,679; Mar. 10, 1986; 1–3 and Exhibits A and B.

Burron's SafSite remove the risk; (Undated); pp. M44956–M44959.

Court of Appeals for the Federal Circuit's Decision in *Baxter International vs. McGaw Inc.*, 47 USPQ2D 1225 (Fed. Cir. 1998).

* cited by examiner

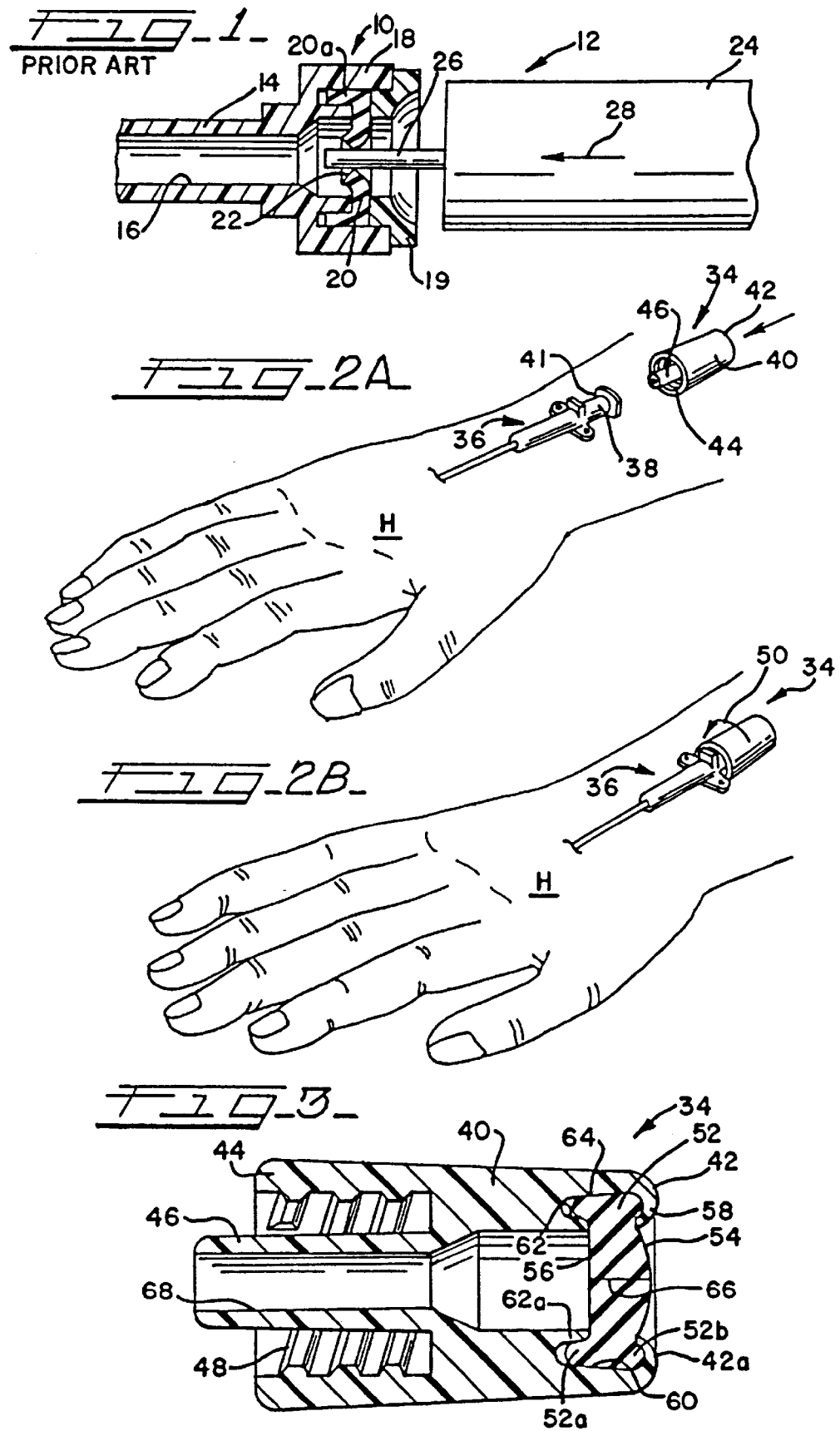

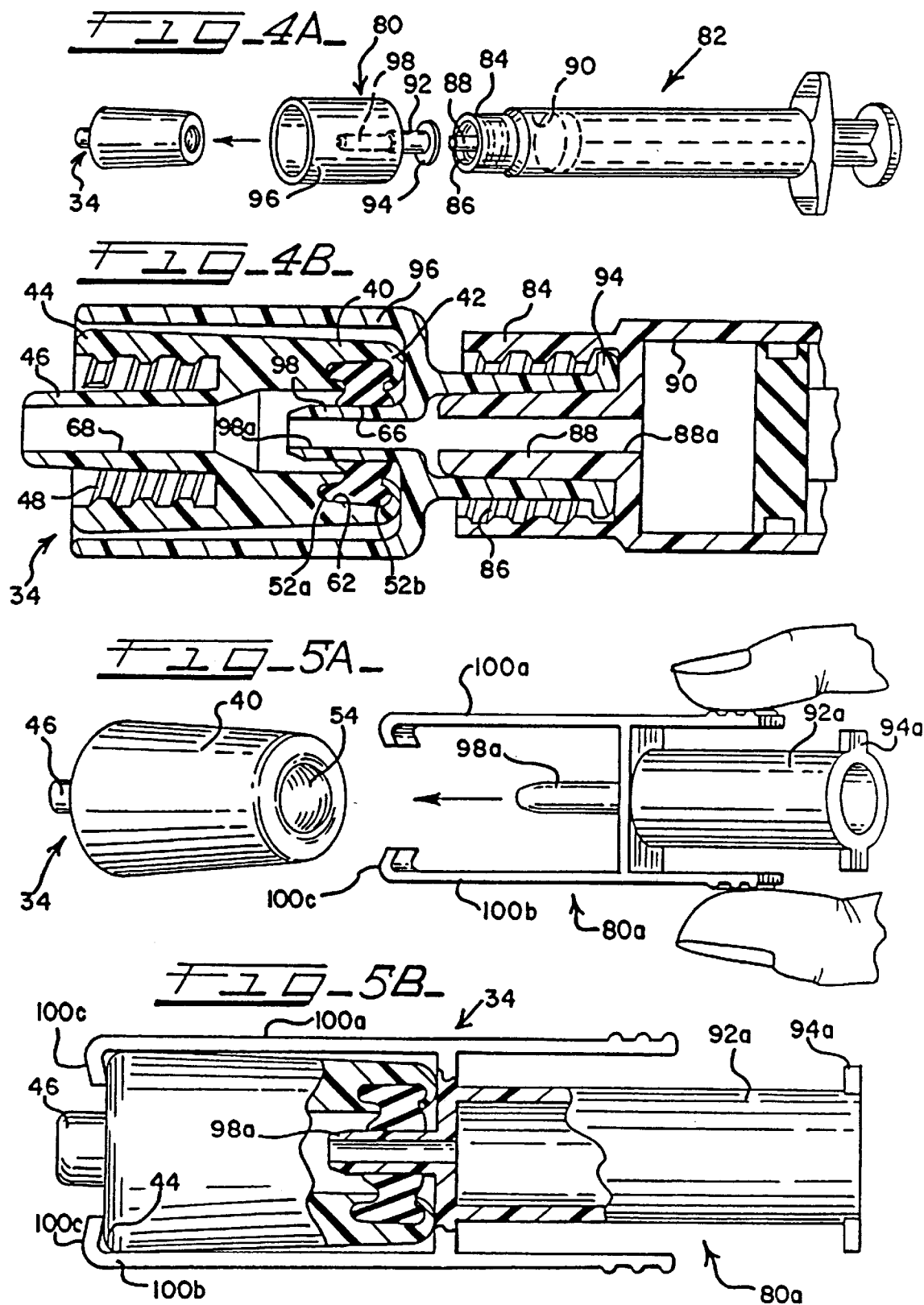

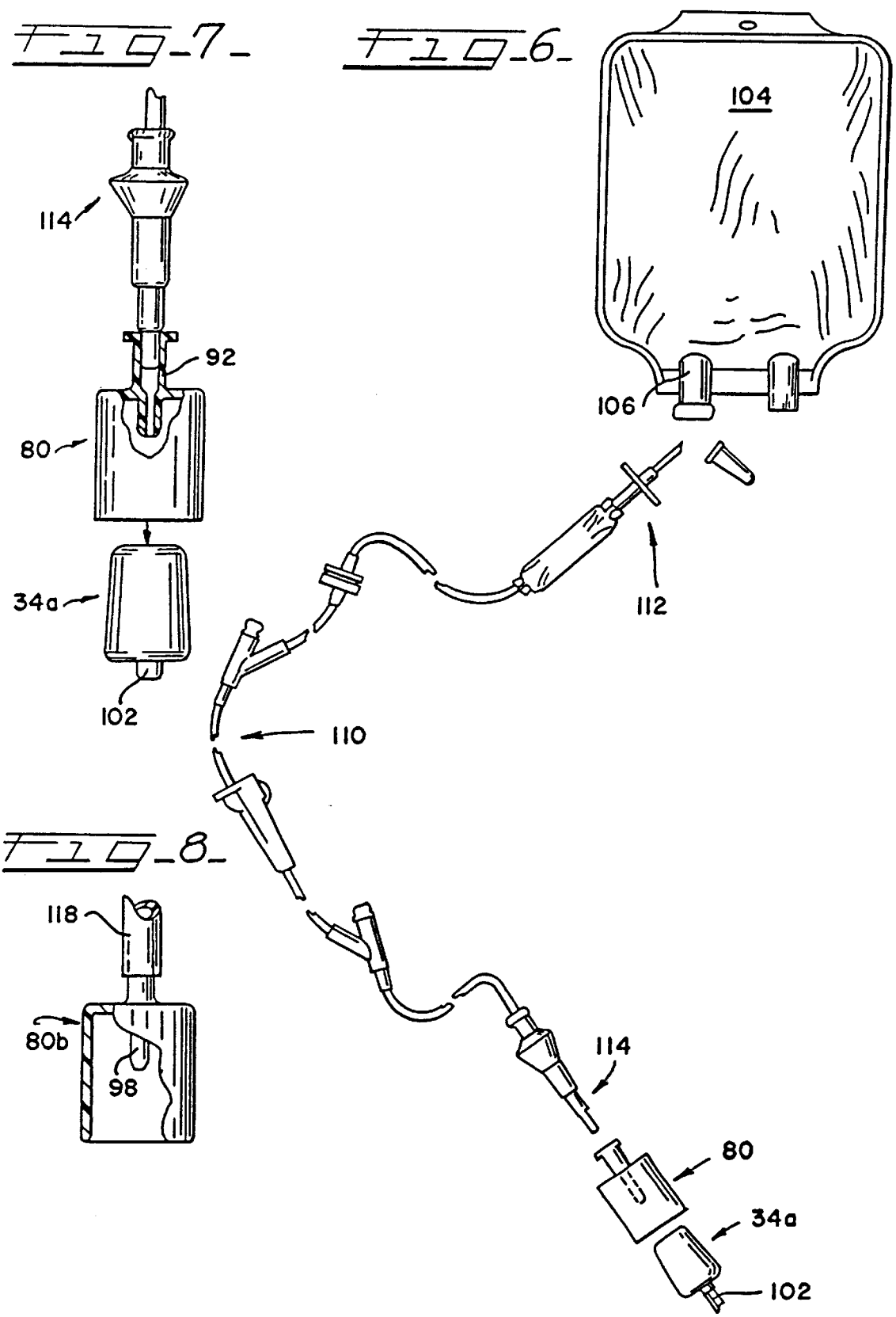

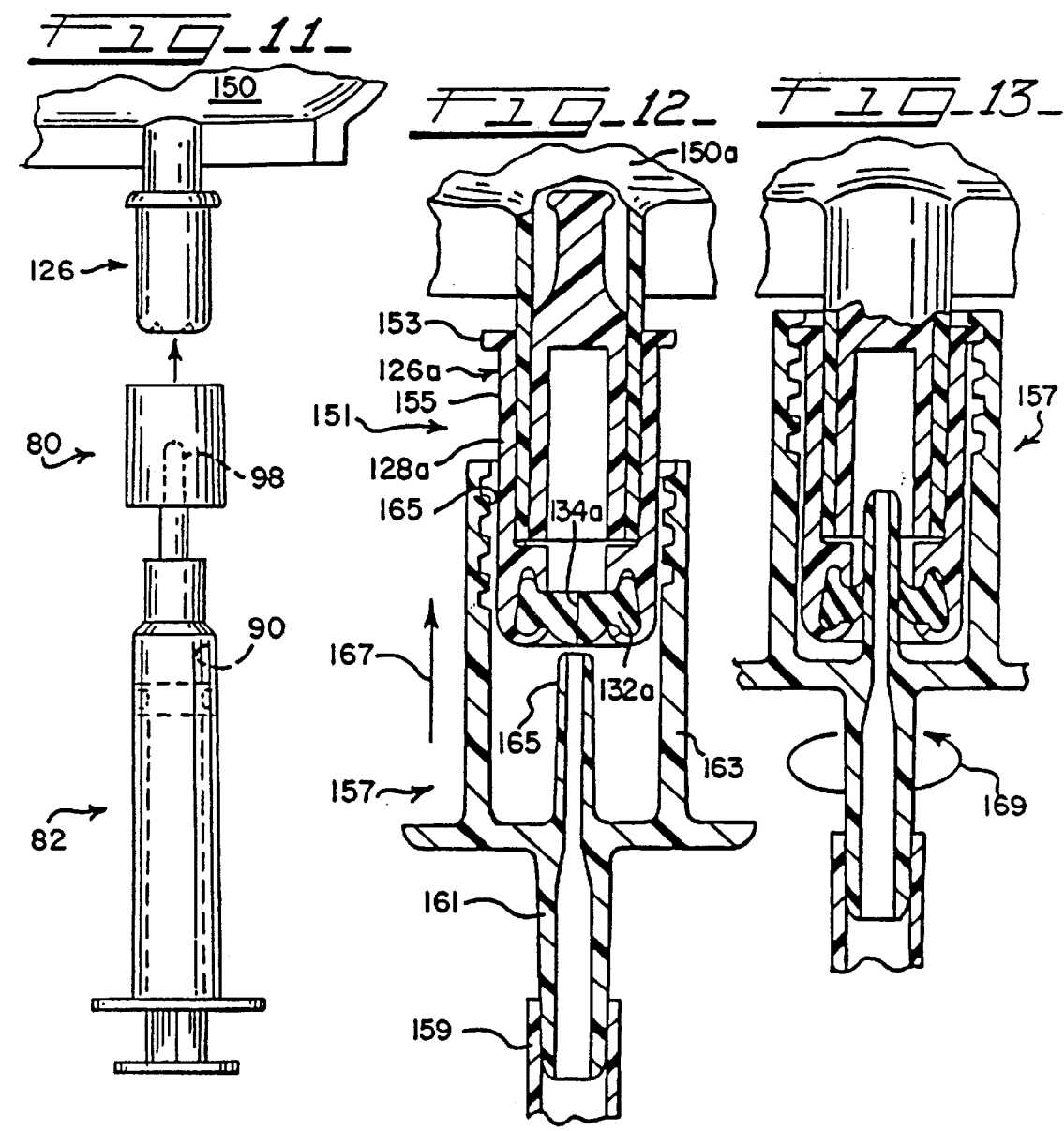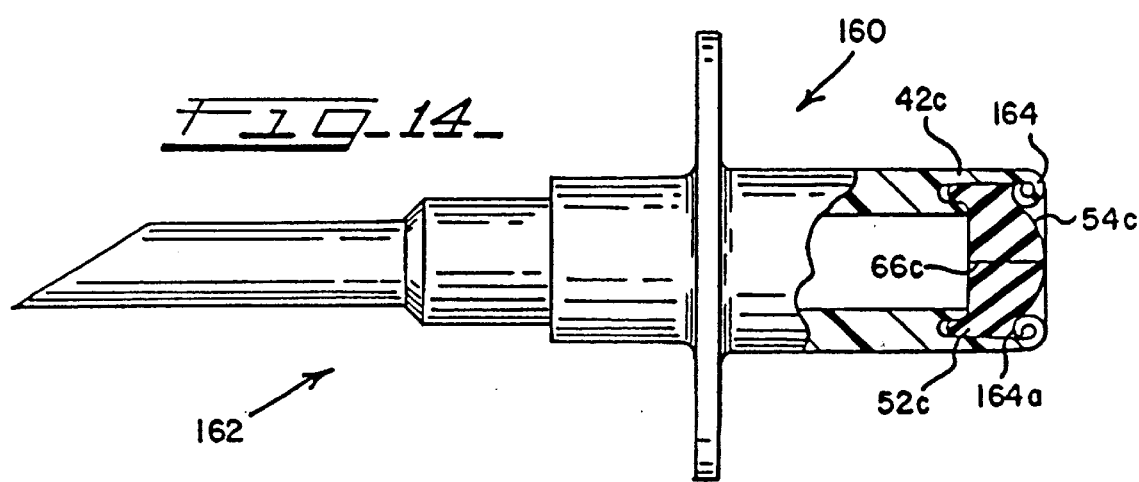

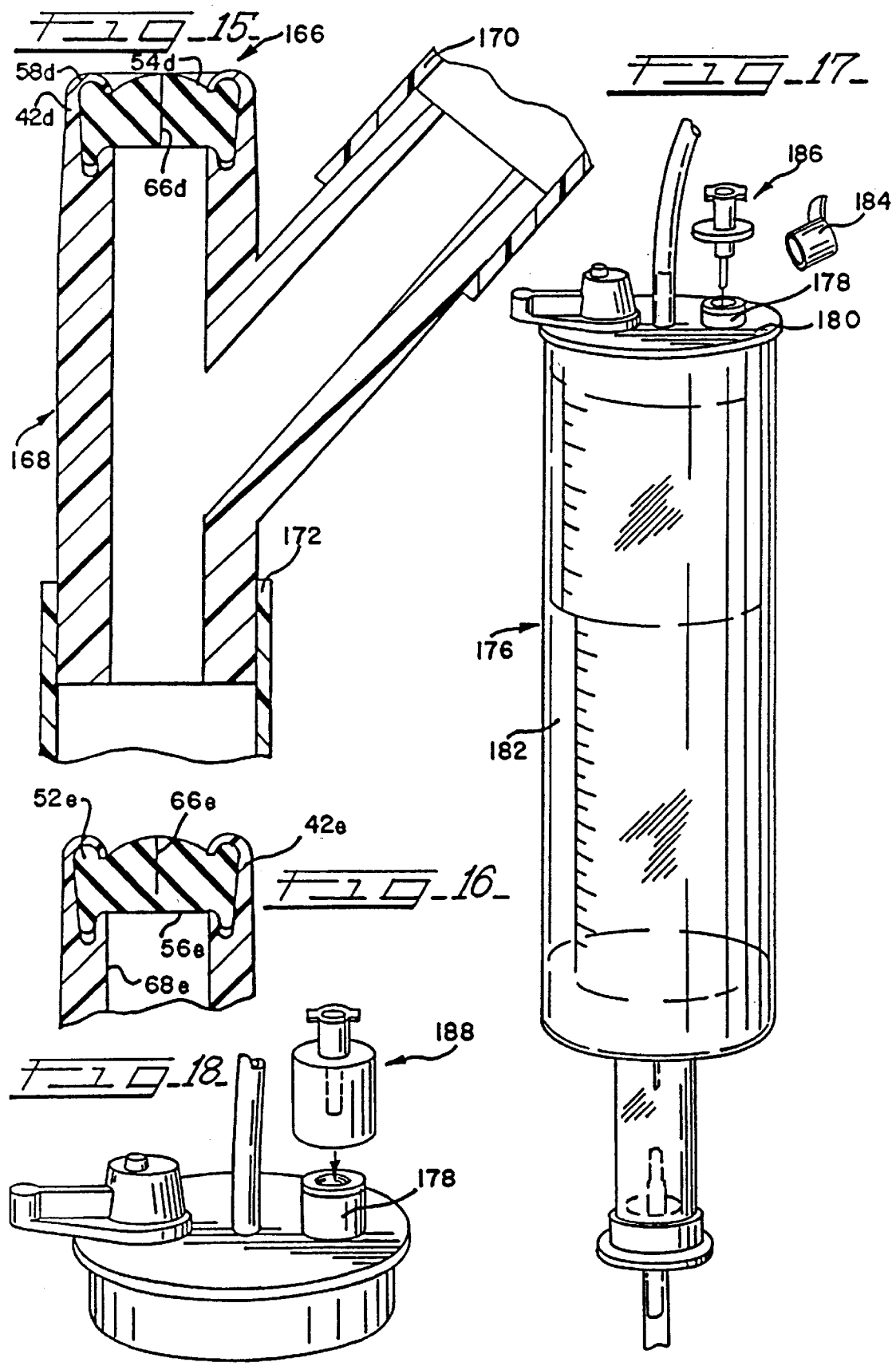

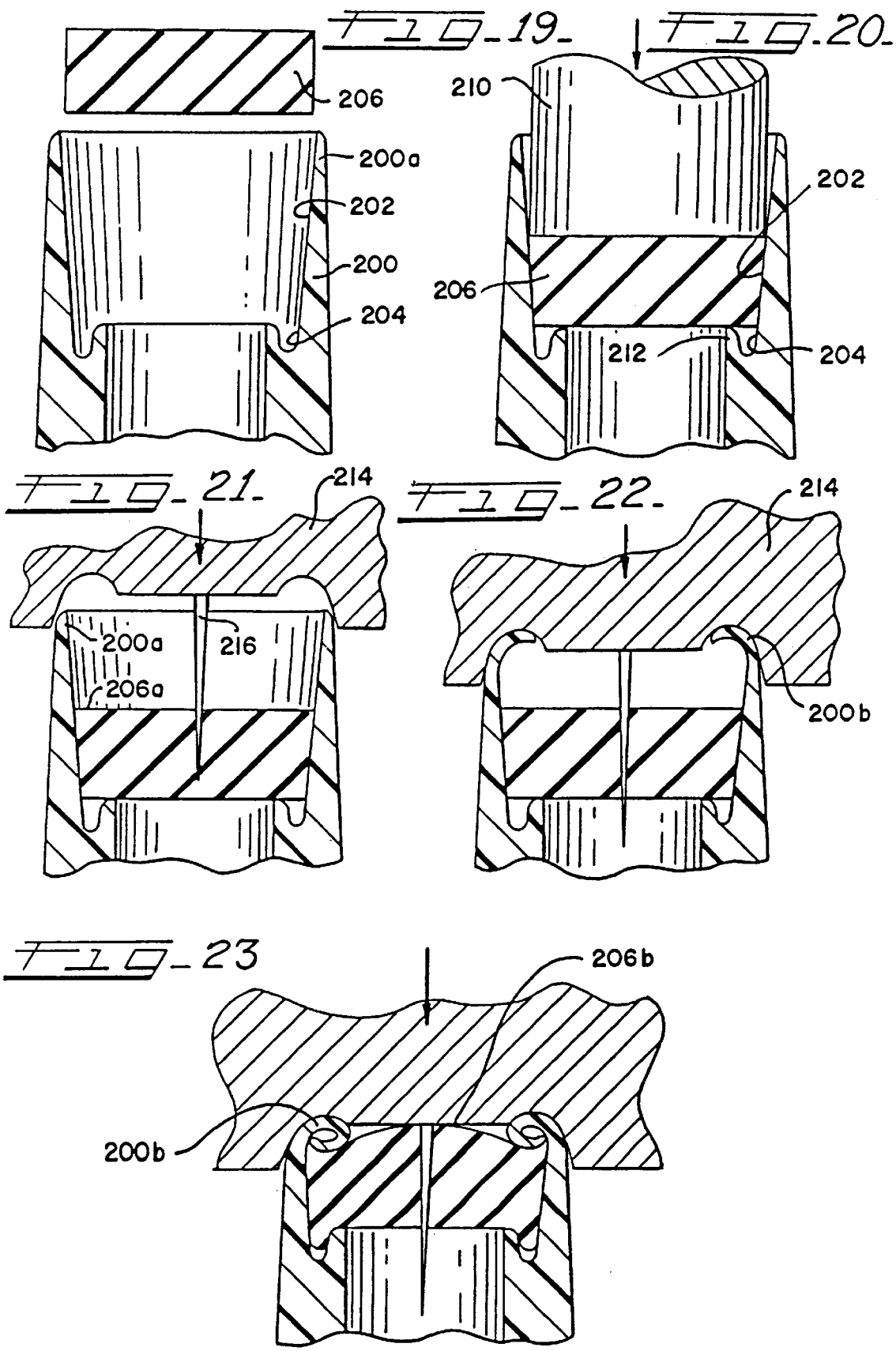

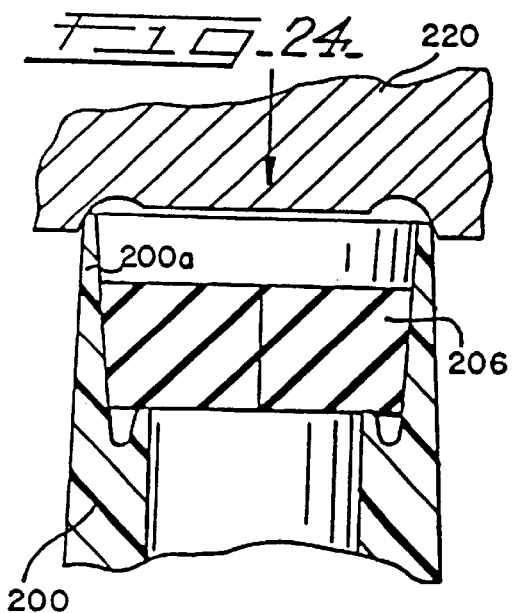
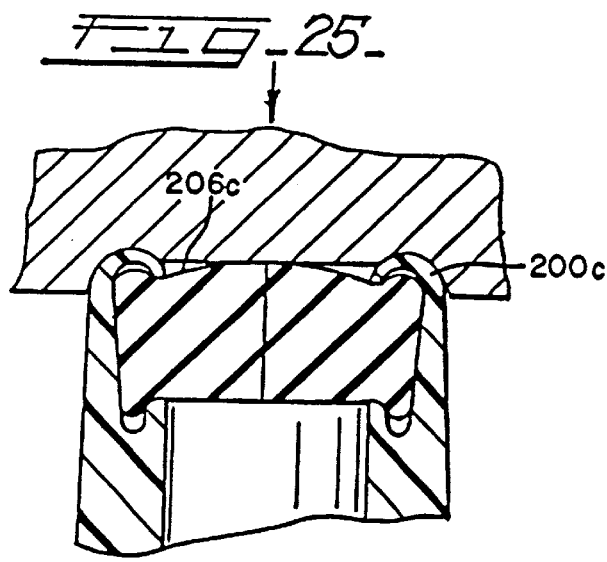
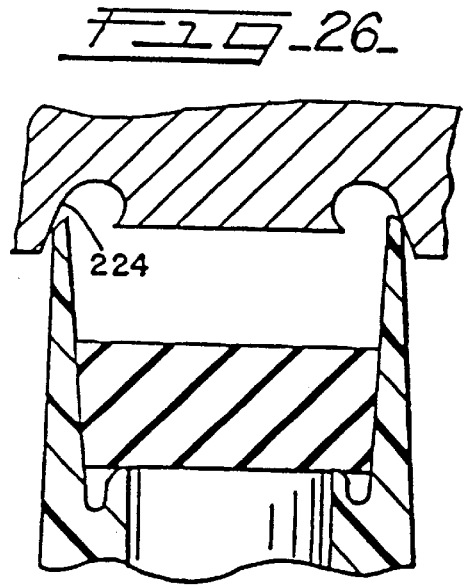
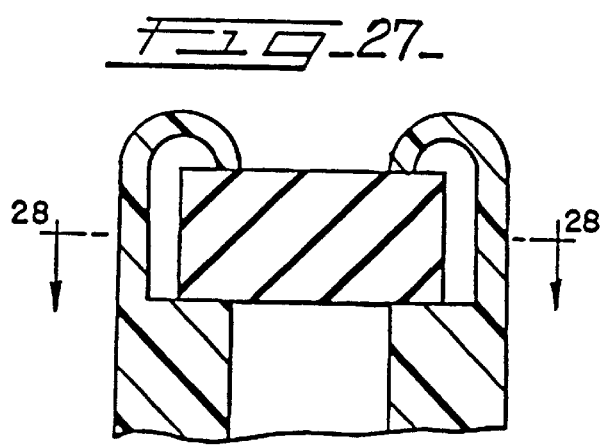
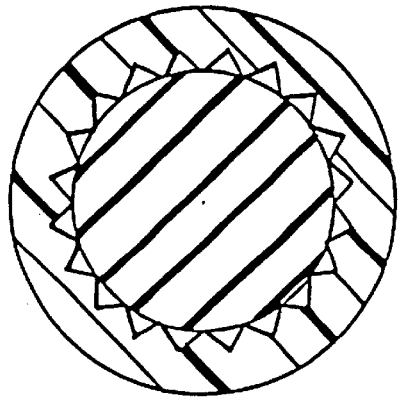

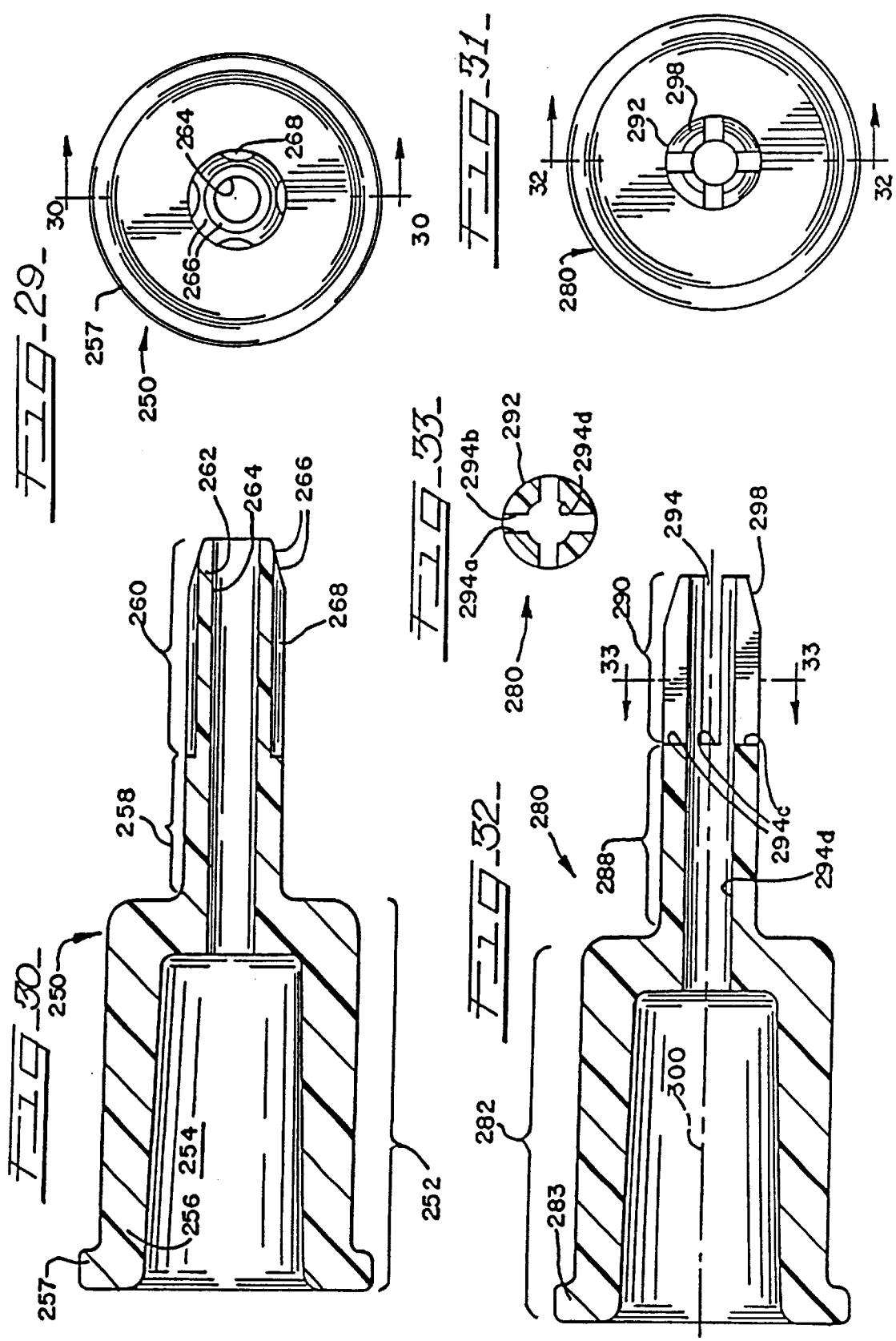

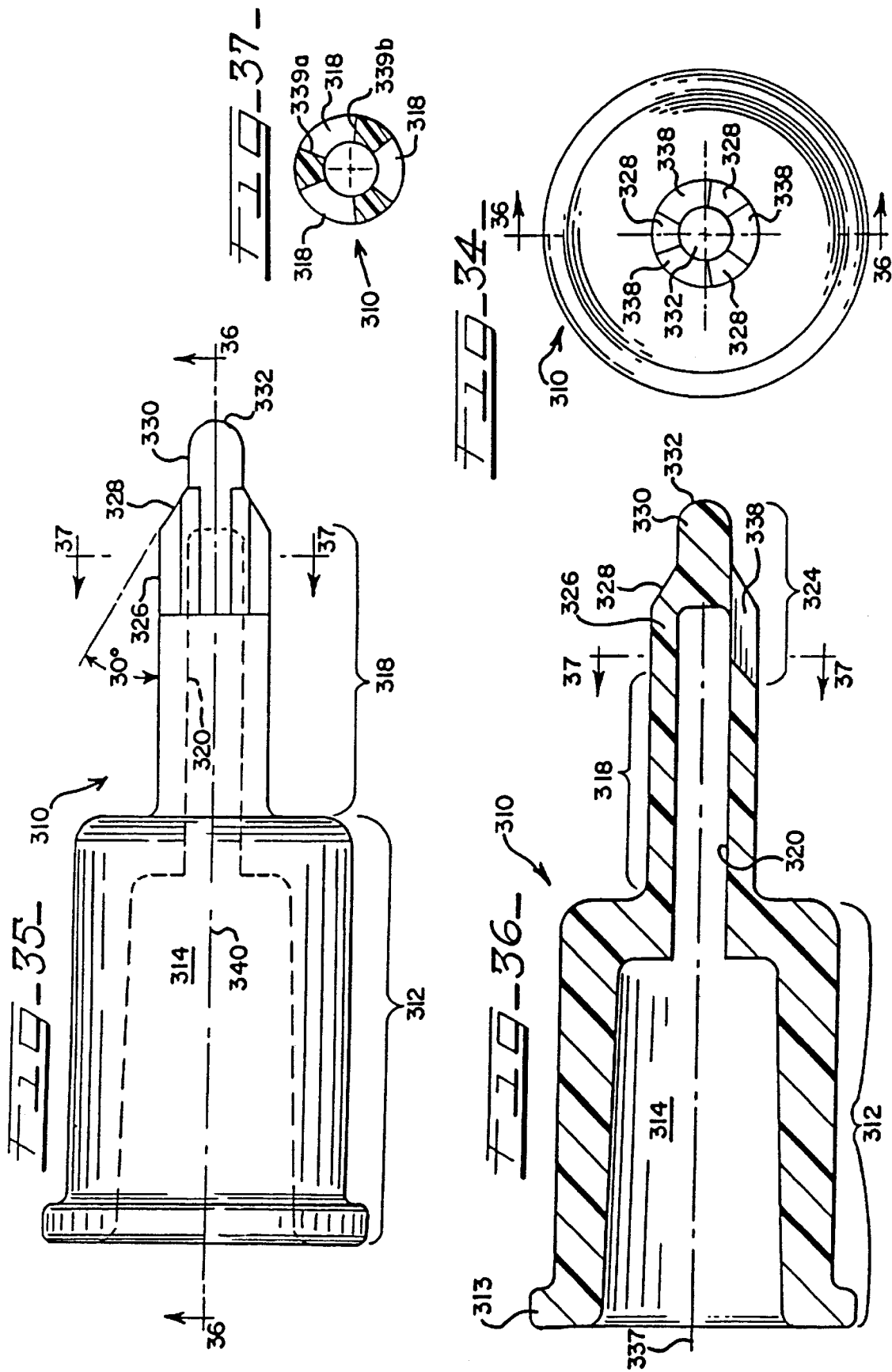

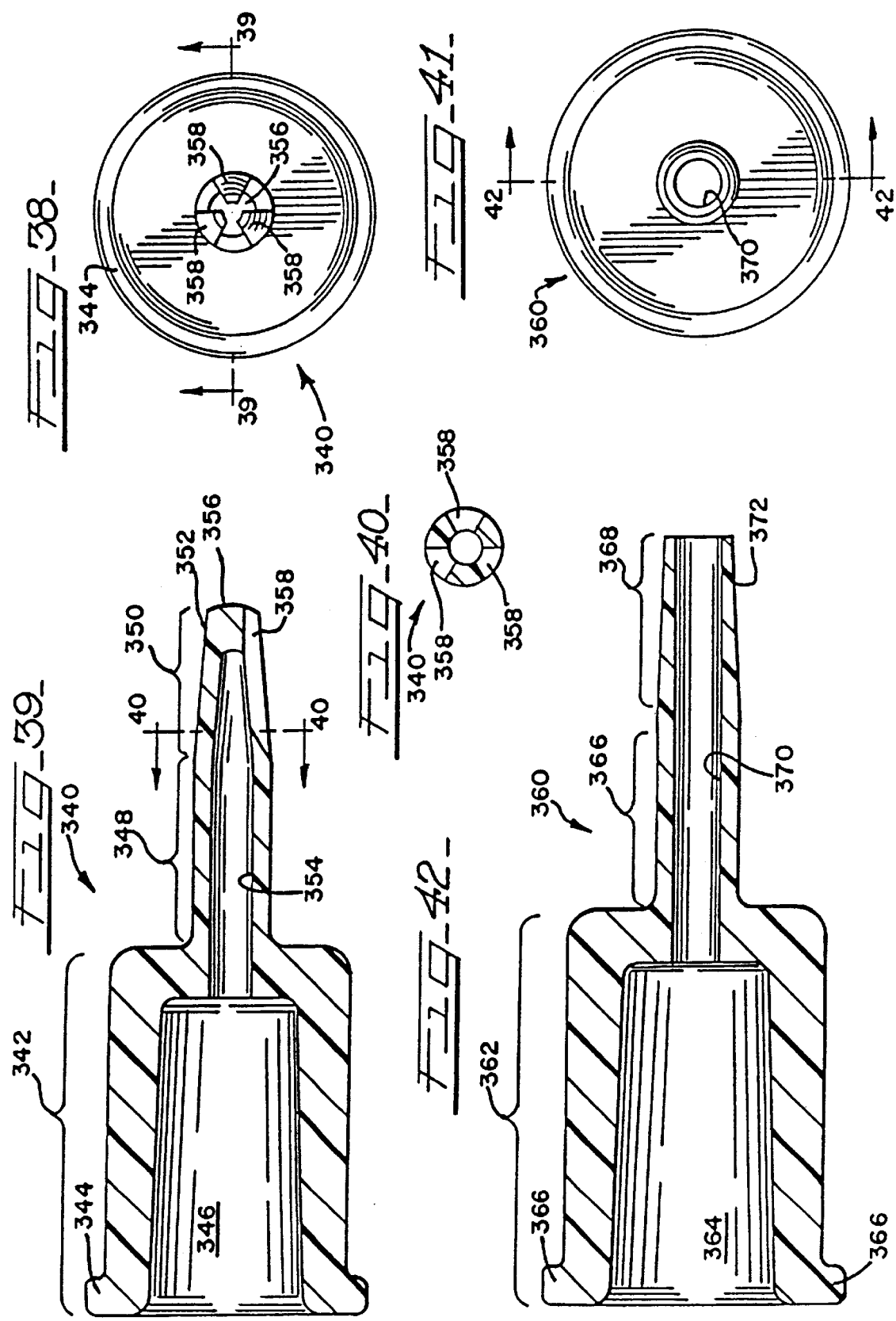

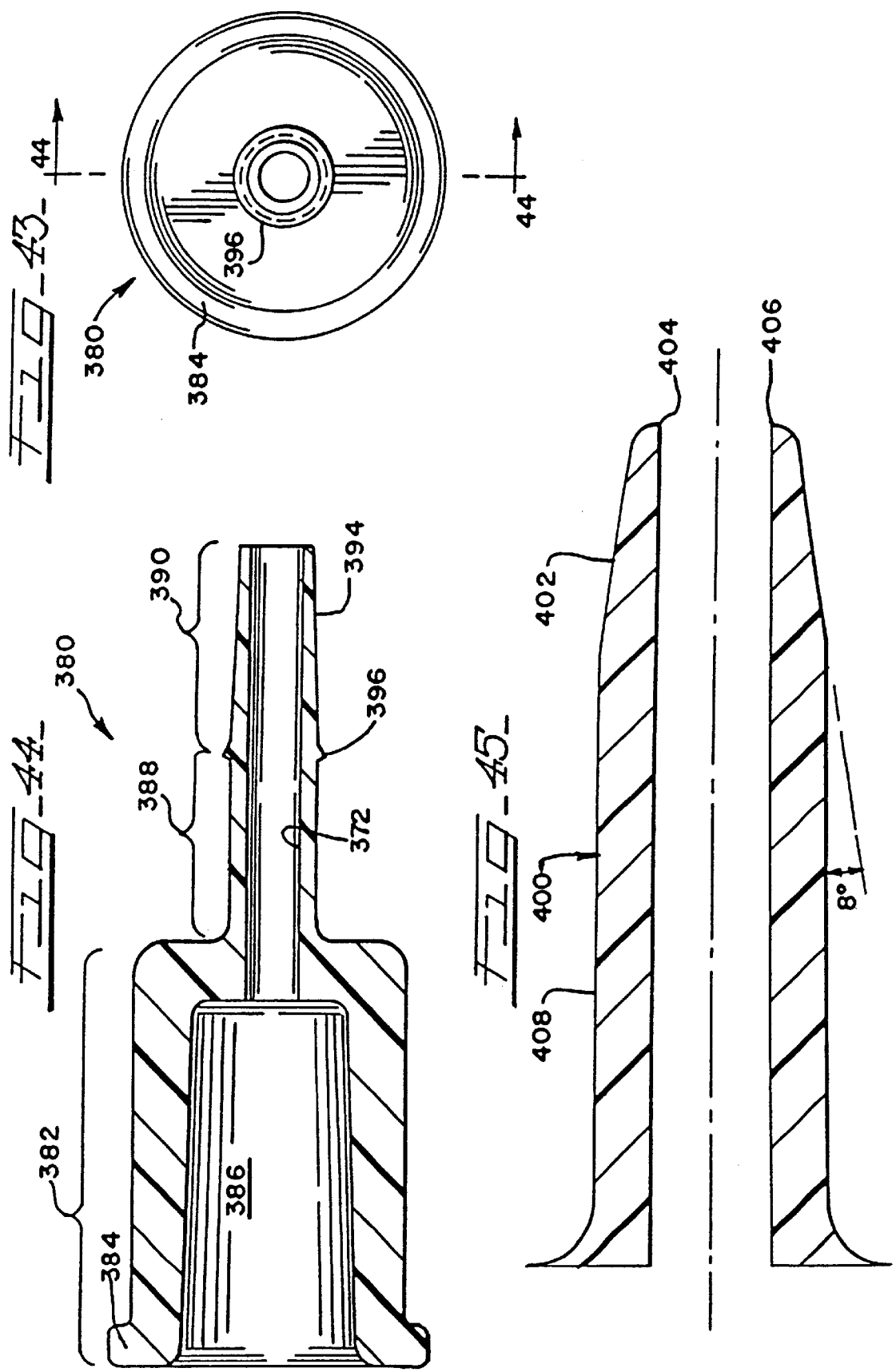

PRE-SLIT INJECTION SITE AND TAPERED CANNULA

This is a continuation-in-part of U.S. patent application Ser. No. 07/217,004, filed Jul. 8, 1988 now abandoned, which is a continuation-in-part of U.S. patent application Ser. No. 07/147,414, filed Jan. 25, 1988, now abandoned.

This application is a continuation of 09/181,975 filed Oct. 29, 1998 U.S. Pat. No. 6,261,266 which is a con of 8/695,040 filed on Aug. 9, 1996 U.S. Pat. No. 5,899,888 which is a con of 07/325,617 filed Mar. 17, 1989.

FIELD OF THE INVENTION

The invention pertains to coupling systems usable to transfer materials from one flow conduit to another. More particularly, the invention pertains to two-part coupling members with a first part including a pre-slit septum and second part including a blunt cannula. The pre-slit septum slidably receives the blunt cannula to effect the coupling.

BACKGROUND OF THE INVENTION

Injection sites usable with pointed cannulae have long been known. For example, such sites can be formed with a housing having a fluid flow path therein. A septum is positioned in the housing closing the fluid flow path.

One injection site usable with a piercing cannula is disclosed in U.S. Pat. No. 4,412,573 to Zbed entitled "Injection Site." The Zbed patent is assigned to the assignee of the present invention.

The pointed cannula can be forced through the septum into fluid flow communication with the flow path in the housing. Known injection sites usable with a piercing cannula can be physically damaged by repetitive piercing caused by the sharp cannula. This damage, known as coring or laceration, can result in subsequent leakage.

Due to problems associated with infectious agents, personnel using such pointed cannulae do so with great care. Notwithstanding careful and prudent practice, from time to time, accidents do occur and individuals using such pointed cannulae jab themselves.

Injection sites usable with a blunt cannula are also known. For example, U.S. Pat. No. 4,197,848 issued to Garrett, et al., entitled "Closed Urinary Irrigation Site" and assigned to the assignee of the present invention discloses one such injection site. That injection site is a relatively low pressure device having a relatively thin, molded, sealing member. The sealing member has an opening therethrough.

A blunt cannulae can be forced through the sealing member placing the cannulae into fluid flow communication with a fluid flow pathway in the injection site.

Injection sites of the type noted above usable with a blunt cannula have the advantage that the blunt cannula will not pierce the skin of a user. On the other hand, it is important that the pre-slit injection site reseal with enough force that fluids do not ooze therefrom and that airborne particulate matter, bacterial or viral matter do not enter therethrough.

Hence, there continues to be a need for a pre-slit injection site which can be used with a variety of solutions and over a range of fluid pressures. Further, there continues to be a need for such a pre-slit injection site which will reliably reseal even after many insertions of the blunt cannula.

Such an injection site should be able to receive a large number of insertions of the cannula without displaying reseal failure. Such an injection site should provide for improved alignment of the cannula on insertion. Improved alignment will result in less chance of damage to the injection site after repeated insertions of the cannula. Preferably, the injection site would also be usable with a pointed cannula. Preferably, a pre-slit injection site usable with a blunt cannula will provide a reasonable level of insertion force such that health care personnel will readily be able to insert the blunt cannula, yet the cannula will not easily fall from or drop out of contact with the septum.

SUMMARY OF THE INVENTION

In accordance with the invention, an easily wipeable injection site usable with a blunt cannula is provided. The injection site includes a housing which defines a fluid flow channel therethrough. The housing has a first and a second end.

A flexible sealing member is carried by the housing for sealing the first end. The sealing member has a resealable opening therein. The sealing member also is formed with a curved exterior peripheral surface such that the blunt cannula can be sealingly inserted through the opening and placed in fluid flow communication with the flow path. Further, the blunt cannula can be removed from the opening with a sealing member then interacting with the housing so as to reseal the opening.

The housing can also be formed with the first end including an annular channel underlying the sealing member. The sealing member is subjected to radially directed forces by a tapered surface of the first end of the housing. These forces tend to reseal the opening in the sealing member.

The sealing member can be a cylindrically shaped rubber member. The first end of the housing can include an interior tapered surface for receiving the sealing member and for applying the radially directed forces to the sealing member.

A retaining member carried by the first end of the housing can be used to retain the sealing member within the housing. The retaining member can be generally U-shaped. Alternately, the retaining member can be formed as a coiled spring.

The retaining member applies axially directed forces to the sealing member. In one embodiment of the invention, the retaining member deflects the sealing member and forms a curved exterior peripheral surface thereon. The curved exterior peripheral surface is an easily wipeable surface.

The retaining member deflects or distorts the upper and lower peripheral edges slightly as a result of applying axial forces thereto. When the blunt cannula is inserted into the slit in the sealing member, an annular interior peripheral region of the sealing member deforms further and fills, at least in part, the annular channel.

Deformation of this annular peripheral region results in an insertion force in a range of 2.0 pounds (0.7564 kilograms) to 5.0 pounds (1.891 kilograms). Preferably, the insertion force will have a value of the order of 2.0 pounds (0.7564 kilograms).

The resealable opening in the sealing member can extend entirely through that member. Alternately, the resealable opening can extend only partway therethrough. In this embodiment, the end of the blunt cannula will be used to tear through the remainder of the sealing member.

The sealing member can be formed in two parts. An exterior cylindrical portion can be slit completely. An interior cylindrical unslit portion can be provided to seal the site until the blunt cannula is inserted therethrough the first time.

The interior surface of the first end can be formed with the taper in a range on the order of 5 degrees to 20 degrees.

Preferably, the interior surface will have a taper on the order of 12 degrees. This tapered surface permits the use of a cylindrically shaped sealing member.

To provide for leak-free insertion, the length of the slit in the sealing member must be less than one-half the circumference of the cannula being inserted therethrough. Hence, the slit length may exceed the diameter of the cannula being inserted. In addition, the slit length must be great enough, given the elastic limit of the sealing member, to prevent tearing during insertion.

Further, in accordance with the invention, a coupling system for coupling first and second fluid flow members together is provided. The coupling system includes an injection site which is affixed to the first fluid flow member. The injection site includes a housing. The housing has a fluid flow path therethrough.

A sealing member is carried by the housing. The sealing member has a resealable opening therein.

An annular retaining member is carried by the housing and cooperates with the housing to retain the sealing member therein. Radially directed forces are applied to the sealing member by the housing, thereby urging the opening into a resealed condition.

A blunt cannula, affixed to second fluid flow member, has a fluid flow path therethrough. The cannula carries a locking member for lockingly engaging the housing when the cannula extends through the opening of the sealing member. When so positioned, the two fluid flow members are placed into fluid flow communication.

The locking member can include a luer-type twist lock fitting. Alternately, the locking member can include slidably engageable members which are responsive to axial movement of the injection site and the cannula toward one another.

In accordance with further aspects of this invention, the blunt cannula may be provided with features that facilitate insertion into the injection site, enhance fluid flow or dispersion, increase tug resistance, and reduce kickback.

In particular, one embodiment of the cannula includes a tube with a plurality of elongate discharge slots adjacent the distal end. The fluid changes direction as it passes laterally through the slots and out of the tube. The flow area of the slots exceeds the flow area inside the tube. This slot structure enhances fluid flow and inspersion characteristics. In addition, the slots decrease the contact surface area on the tube exterior so as to facilitate insertion.

In a further modification, the cannula includes a lead post on the tube distal end to guide the cannula through the slit in the injection site.

In another cannula embodiment, the tube is generally cylindrical and the fluid discharges directly from an open end of the tube. The exterior surface of the tube is provided with grooves to reduce the contact surface area.

In still another cannula embodiment, the tube has a cylindrical portion and a tapered distal end portion which are each about equal in length. The taper facilitates insertion, and the remaining cylindrical portion reduced kickback.

In yet another embodiment, the cannula includes an annular barb which functions to reduce kickback.

Other advantages of a blunt plastic cannula in accordance with the invention, relative to conventional steel needles include a higher fluid flow rate capacity and a simpler one-piece plastic design.

Numerous other advantages and features of the present invention will become readily apparent from the following detailed description of the invention and the embodiments thereof, from the claims and from the accompanying drawings in which the details for the invention are fully and completely disclosed as a part of this specification.

BRIEF DESCRIPTION OF THE DRAWINGS

FIG. 1 is a side elevational view, partly in section, of a prior art pre-slit injection site and an associated blunt cannula;

FIG. 2A is a view in perspective of a catheter positioned in the hand of a patient with a pre-slit injection site in accordance with the present invention positioned adjacent thereto;

FIG. 2B is a perspective view of the catheter of FIG. 2A with a pre-slit injection site in accordance with the present invention rotatably affixed thereto;

FIG. 3 is an enlarged side elevational view in a section of a pre-slit injection site in accordance with the present invention formed on a body having a luer twist-lock type connector for coupling to a catheter;

FIG. 4A is an exploded view of a pre-slit injection site, a shielded blunt cannula and a syringe prior to being coupled together;

FIG. 4B is an enlarged, side elevational view in section of the pre-slit injection site, the shielded blunt cannula and the syringe of FIG. 4A coupled together to form a sealed fluid flow system;

FIG. 5A is a view in perspective of a pre-slit injection site prior to engaging a blunt cannula carrying a locking member;

FIG. 5B is an enlarged side elevational view, partly broken away, illustrating the interrelationship between the pre-slit injection site and the blunt cannula of FIG. 5A;

FIG. 6 is an overall view of a container, an associated solution administration set and a pre-slit injection site in accordance with the present invention;

FIG. 7 is an enlarged side elevational view, partly broken away illustrating the relationship between selected elements of FIG. 6;

FIG. 8 is a side elevational view, partly broken away illustrating an alternate shielded cannula in accordance with the present invention;

FIG. 11 is a side elevational view of the injection site and the fragmentary container of FIG. 10 prior to being engaged with a shielded cannula carried by a syringe;

FIG. 12 is an enlarged side elevational view, partly in section, of a coupling system with a pre-slit injection site partly coupled to a blunt cannula;

FIG. 13 is an enlarged side elevational view, partly in section, of the coupling system of FIG. 12 subsequent to engagement of the two coupling members;

FIG. 14 is a side elevational view, partly broken away, of a spike connector carrying a pre-slit injection site in accordance with the present invention;

FIG. 15 is an enlarged side elevational view of a Y-connector in section carrying a pre-slit injection site in accordance with the present invention;

FIG. 16 is an enlarged fragmentary side elevational view in section of a coupling member carrying a pre-slit injection site where the slit extends only partway through the septum;

FIG. 17 is a perspective view of a burette solution administration set carrying a pre-slit injection site in accordance with the present invention;

FIG. 18 is a view of part of a burette solution administration set carrying a pre-slit injection site being coupled to a shielded blunt cannula;

FIG. 19 is a step in the method of making a pre-slit injection site in accordance with the present invention;

FIG. 20 is another step in the method of making a pre-slit injection site in accordance with the present invention;

FIG. 21 is an initial phase of a final step in making a pre-slit injection site in accordance with the present invention;

FIG. 22 is an intermediate phase of the final step in a method of making a pre-slit injection site in accordance with the present invention;

FIG. 23 is a final phase of the final step in a method of making a pre-slit injection site in accordance with the present invention;

FIG. 24 illustrates an initial phase in an alternate step of making a pre-slit injection site in accordance with the present invention;

FIG. 25 illustrates a final phase of the alternate step in a method of making an injection site in accordance with the present invention;

FIG. 26 illustrates yet another alternate step in a method of making a pre-slit injection site in accordance with the present invention;

FIG. 27 is an enlarged, fragmentary cross-sectional view of another embodiment of an injection site in accordance with the present invention;

FIG. 28 is a cross-section view taken generally along the plane 28—28 in FIG. 27;

FIG. 29 is an end view of another embodiment of the cannula in accordance with the present invention;

FIG. 30 is a cross-section view taken generally along the plane 30—30 in FIG. 29;

FIG. 31 is an end view of another embodiment of the cannula in accordance with the present invention;

FIG. 32 is a cross-sectional view taken generally along the plane 32—32 in FIG. 31;

FIG. 33 is a cross-sectional view taken generally along the plane 33—33 in FIG. 32;

FIG. 34 is an end view of another embodiment of the cannula in accordance with the present invention;

FIG. 35 is a fragmentary, side elevational view of the embodiment of the cannula illustrated in FIG. 34;

FIG. 36 is a cross-sectional view taken generally along the plane 36—36 in FIG. 34;

FIG. 37 is a cross-sectional view taken generally along the plane 37—37 in FIG. 36;

FIG. 38 is an end view of another embodiment of the cannula according to the present invention;

FIG. 39 is a cross-sectional view taken generally along the plane 39—39 in FIG. 38;

FIG. 40 is a cross-sectional view taken generally along the plane 40—40 in FIG. 39;

FIG. 41 is an end view of another embodiment of the cannula according to the present invention;

FIG. 42 is a cross-sectional view taken generally along the plane 42—42 in FIG. 41;

FIG. 43 is an end view of another embodiment of the cannula according to the present invention;

FIG. 44 is a cross-sectional view taken generally along the plane 44—44 in FIG. 43; and FIG. 45 is a view in section of another insertion member for a blunt cannula.

DETAILED DESCRIPTION OF THE PREFERRED EMBODIMENTS

Figure 9:
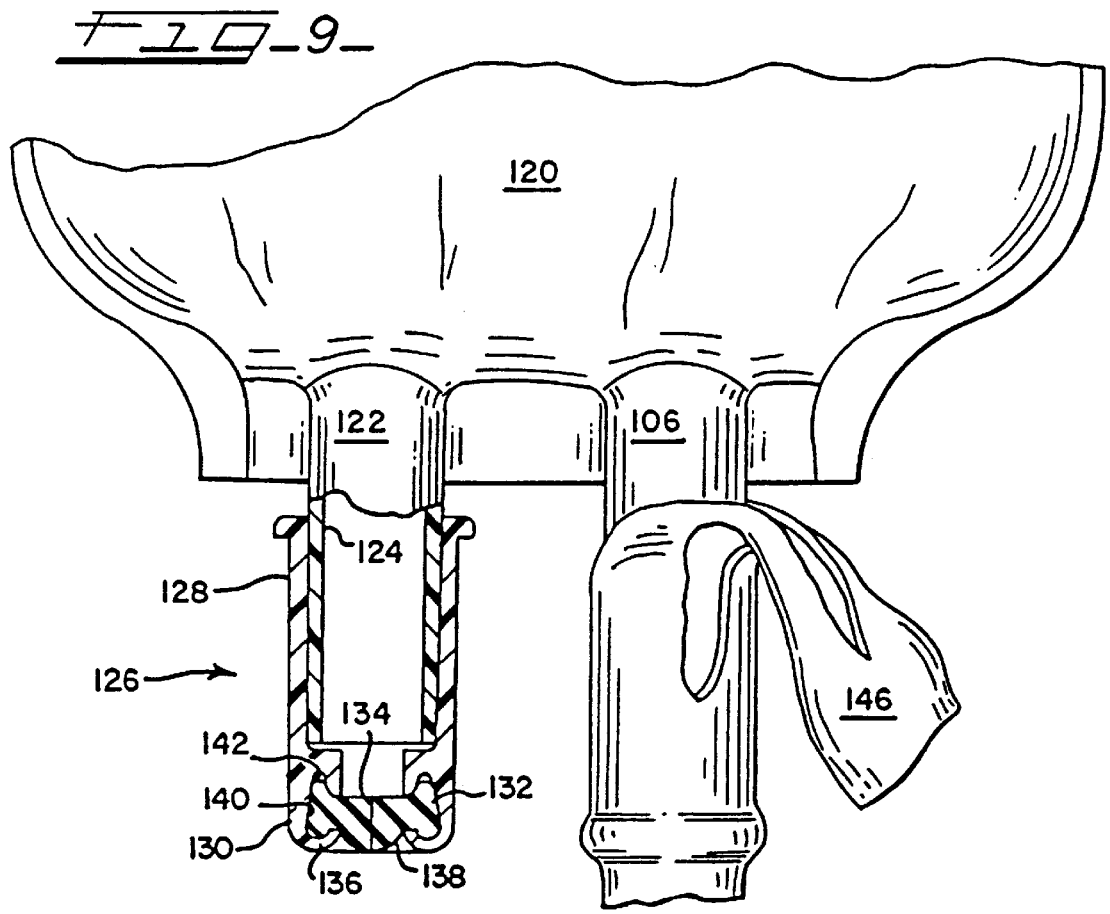
FIG. 9 is a side elevational view, partly in section, of a pre-slit injection site mounted on a fragment of a solution container.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

A prior art pre-slit injection site 10 and associated blunt cannula 12 are illustrated in FIG. 1. The prior art injection site 10 has a cylindrical housing 14 with a fluid flow path 16 therethrough. A first end 18 of the housing 14 is closed with a relatively thin disc-shaped resealable member 20. The member 20 has a resealable opening 22 therein.

The member 20 is a molded septum with an integrally formed skirt 20a. The skirt 20a is oriented generally perpendicular to the portion of the septum with the opening 22.

The cannula 12 includes a body portion 24 which carries at a first end a hollow, cylindrical, blunt piercing member 26. As the cannula 12 is moved in a direction 28 toward the first end 18 of the injection site 10, the member 26 slidably engages the opening 22. The sealing member 20 is then deformed adjacent the opening 22 and the number 26 extends into the flow path 16. A fluid flow path through the cannula 12 will then be in fluid flow communication with the flow path 16 via the hollow piercing member 26.

In contradistinction to the prior art pre-slit injection site 10 of FIG. 1, FIGS. 2A and 2B illustrate a pre-slit injection site 34 being coupled to a peripheral venous catheter 36. The catheter 36 is shown in fluid flow communication with a vein in a hand H of a patient. The catheter 36 carries at a proximal end 38 a luer-type female twist lock connector 41.

The pre-slit injection site 34 is formed with a cylindrical housing 40 having a first end 42 and a second end 44.

Carried by the housing 40, adjacent the second end 44 is a hollow cylindrical fluid flow member 46. The member 46 slidably engages a receiving member in the housing 38 of the catheter 36, thereby providing a sterile fluid flow coupling as is well known and conventional.

A plurality of internal male luer-type threads 48 is carried by the housing 40 adjacent the second end 44. The threads 48 will engage the flange member 41 when the injection site 34 is rotated in a direction 50. When so coupled together, the catheter 36 and the injection site 40 provide a sealed coupling through which fluids may be injected into the vein of the hand H.

FIG. 3 illustrates, in section, further details of the injection site 34. A resealable septum 52 is carried by the first end 42 of the housing 40. The septum 52 includes first and second spaced apart surfaces 54 and 56 respectively. The surface 54 has been forced into a dome-like shape by annular, U-shaped, swaged end members 58 carried by the first end 42. The dome-like shape of the surface 54 can extend beyond a surface 42a of the first end 42. This facilitates cleaning the surface 54.

The septum 52 has a generally cylindrical shape. The septum 52 can be formed of a latex or synthetic rubber material. Alternately, the septum can be formed of a thermoplastic elastomer. The material used for the septum 52 should be non-toxic and sterilizable such as by means of radiation, steam or Ethylene Oxide.

Because the septum 52 is generally cylindrical in shape, it can be die-cut from a sheet, cut from an extruded rod or molded. The septum 52 can have an exemplary diameter on the order of 0.30 inches (0.762 centimeters). The height of the septum 52 can be, for example, on the order of 0.125 inches (0.3175 centimeters).

The first end 42 is also formed with a tapered interior surface 60 which terminates in an annular channel 62. The tapered interior surface 60 has a taper in a range of 5 degrees to 20 degrees. Preferably, the taper will be on the order of 12 degrees. With the indicated size of the above noted exemplary septum 52 and a 12 degree taper, diametric resealing compression of the septum 52 adjacent the channel 62 is on the order of 10%.

The channel 62 is bounded in part by a septum supporting ridge 62a. The channel 62 can typically have a depth in a range of 0.050–0.070 inches (0.127–0.1778 centimeters).

A peripheral surface 64 of the septum 52 slidably engages the tapered interior surface 60 as the septum 52 slides into the first end 42. The annular channel 62 which underlies the interior peripheral surface 56 of the septum 52 is provided to permit the septum 52 to deform when a blunt cannula is inserted through an opening 66 therein.

The housing 40 is also formed with a fluid flow path 68 such that fluids injected via a blunt cannula inserted through the resealable opening 66 can flow into the catheter 36 for delivery to hand H of the patient.

The swaged end members 58 apply axial forces to the septum 52 thereby creating the domed exterior peripheral surface 54. The axial forces applied by the end members 58 slightly deform the regions 52a and 52b. In contradistinction, the tapered internal surface 60 applies radially directed forces to the septum 52, thereby forcing the opening 66 into a resealed condition.

In an alternate embodiment, the surface 52 could be formed as a flat, as opposed to a domed, surface.

Once the injection site 34 is lockingly engaged with the catheter 36, a sealed system is formed through which fluids can be infused into the catheter 36. The resealable septum 52 closes the fluid flow path 68.

FIGS. 4A and 4B illustrate in combination the injection site 34, a blunt shielded cannula 80 and a syringe of a conventional type 82. The syringe 82, as is well known, can be formed with a cylindrical hollow end 84 which carries a male luer-type twist lock thread 86. A hollow centrally located cylindrical fluid flow member 88 is in fluid flow communication with an interior region 90 of the syringe 82.

The shielded blunt cannula 80 carries at a first end 92 a female luer twist-lock flange 94. The flange 94 will slidably engage the threads 86 of the end 84. Hence, the shielded blunt cannula 80 can be locked to the syringe 82 forming a closed fluid flow pathway. The shielded cannula 80 could alternately be formed fixedly attached to the syringe 82.

The shielded blunt cannula 80 carries a cylindrical hollow protective shield 96 which surrounds a centrally located hollow, elongated cylindrical blunt piercing member 98. The cylindrical blunt piercing member 98 has a total length on the order of three times the thickness of the septum 52 in order to ensure complete penetration. The cylindrical blunt piercing member 98 has a diameter on the order of ⅓ the diameter of the septum 52. The shield 96 is desirable and useful for maintaining the piercing member 98 in an aseptic condition by preventing touch contamination prior to the shielded cannula 80 engaging the pre-slit septum 52. Also, the shield helps to align the piercing member with the pre-slit septum.

The cylindrical blunt piercing member 98 can slidably engage the pre-slit septum 52, best illustrated in FIG. 4B, thereby extending through the preformed opening 66 therein. As illustrated in FIG. 4B, when the piercing member 98 slidably engages and pierces the septum 52, the region 52a deforms by expanding into and filling, at least in part, the annular channel 62.

The deformation facilitates insertion of the piercing member 98 through the slit 66. Subsequent to the piercing member 98 slidably engaging the injection site 34, the interior region 90 of the syringe 82 is in fluid flow communication with the flow path 68 of the injection site 34 via flow paths 88a and 98a respectively of the syringe and the blunt piercing member 98.

In this engagement condition, the septum 52 seals completely around the piercing member 98. Hence, exterior gases, liquids or airborne matter will be excluded from the channel 68.

Subsequent to infusing fluid from the syringe 82 into the fluid flow pathway 68, hence into the catheter 36 and the hand R of the patient, the syringe 82 with lockingly engaged shielded cannula 80 can be slidably withdrawn from the injection site 34. Subsequent to this withdrawal, the septum 52 reseals the opening 66 therein.

The opening 66 will repeatedly reseal, when the piercing member 98 is removed, provided that the pressure (in the septum 52 of the opening 66) created by interaction of the septum material properties and compression supplied by the housing exceeds the pressure challenge of the fluid contained within. Blunt cannula do not haphazardly core, lacerate, or otherwise damage the sealing interface 66 as conventional needles do, thereby allowing repeatable resealability. However, septum material properties, thickness, and compression allow resealability for a finite number of conventional needle insertions. The combination injection site 34 and catheter 36 then return to its pre-infusion, sealed condition.

FIGS. 5A and 5B illustrate the pre-slit injection site 34 used in combination with a blunt cannula 80a. The cannula 80a includes a hollow body portion 92a with a luer flange 94a, a piercing member 98a, and manually operable elongated locking members 100a and 100b. Alternately, a tubing member could be affixed to the hollow body portion 92.

Curved end regions 100c of the members 100a and 100b slidably engage the second end 44 of the housing 40 when the piercing member 98a of the blunt cannula Boa has been forced through the preformed opening 66, best illustrated in FIG. 5B. The embodiment illustrated in FIGS. 5A and 5B has the advantage that the infusion cannula 80a cannot accidentally disengage from the pre-slit septum 34 during the fluid infusion process. It will be understood that while spring-like deflecting members 100a and 100b are illustrated in FIGS. 5A and 5B that other forms of locking members are within the spirit and scope of the present invention.

FIG. 6 illustrates an alternate pre-slit injection site 34a. A tubing member 102 can be fixedly attached to the cylindrical hollow fluid flow member 46. The embodiment 34a of FIG. 6 utilizes the same structure for the septum 52 including the tapered surface 60 and the underlying annular channel 62 as does the embodiment 34 in FIG. 3. The shielded cannula 80 can be utilized with the injection site 34a as previously described.

In the event that it is desirable to infuse solution from a container 104 with a connectional port 106, a fluid administration set 110 of a conventional variety may be utilized. The set 110 includes a spike connector 112 at a first end. The spike connector 112 is designed to pierce the port 106 of the container 104. The set 110 can also carry a slidably engageable connector 114 of a known type at a second end. As illustrated in FIG. 7, the connector 114 can slidably engage the hollow cylindrical member 92 of the shielded cannula 80, thereby placing the interior fluid of the container 104 into fluid communication with the tubing member 102.

FIG. 8 illustrates yet another alternate 80b to the shielded cannula 80. The piercing member 98 carries a tubing member 118 fixedly attached thereto. The tubing member 118 could be coupled at a second end to a container such as the container 104.

The present pre-slit injection site can be directly affixed to a container 120 as illustrated in FIG. 9. The container 120 includes a rigid hollow cylindrical access port 122 affixed thereto. The access port 122 includes a fluid flow channel 124 in fluid flow communication with the interior of the container 120. Sealingly affixed to the port 122 is a pre-slit injection site 126.

The site 126 includes a cylindrical housing 128 which carries at a first end 130 a septum 132 with a slit 134 formed therein. The first end 130 has been swaged to form an annular U-shaped retaining member 136. The retaining member 136 in turn forms a domed exterior peripheral surface 138 on the septum 132.

The first end 130 also includes a tapered interior force applying surface 140 and an annular channel 142 underlying the septum 132. As discussed previously, the channel 142 provides a space into which the septum 132 can deform when a blunt cannula is forced through the resealable opening 134.

Further, as illustrated in FIG. 9, the injection site 126 can be covered by a removable cover 146 of a type used with the conventional port 106 of the bag 104.

Figure 10:
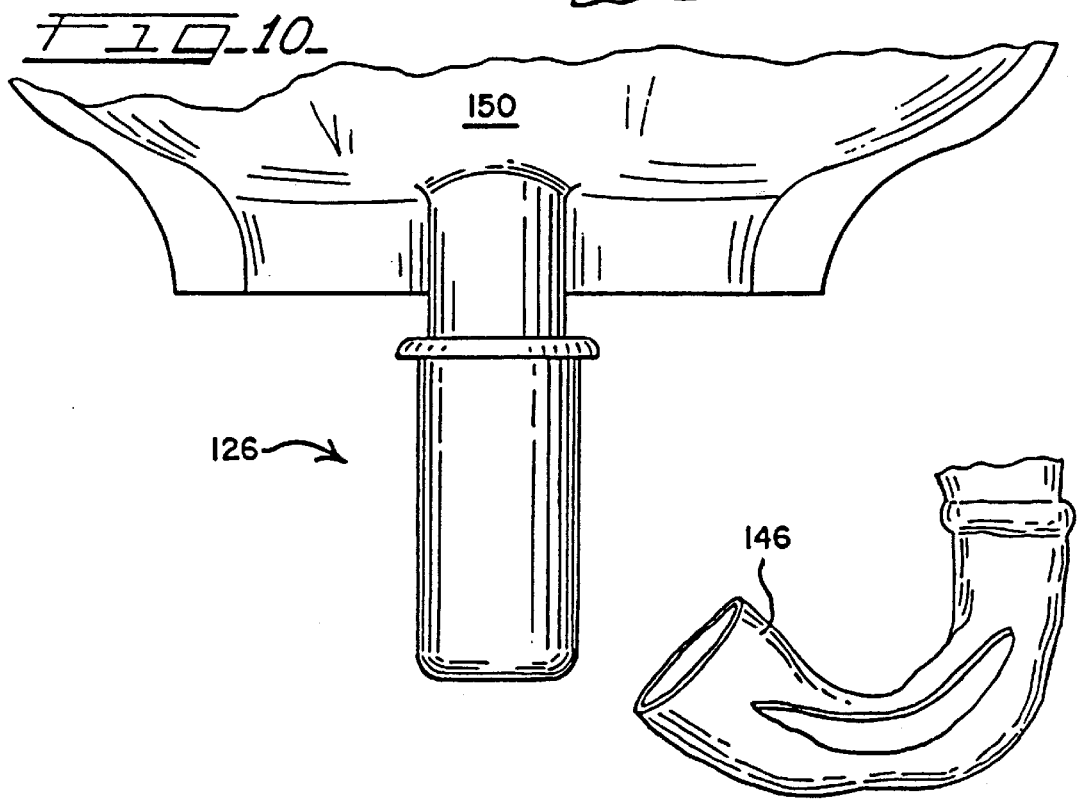
FIG. 10 is a side elevational view of a fragment of a solution container carrying, as a single port, a pre-slit injection site.

While the bag 120 is illustrated formed with two ports, the conventional pierceable port 106 and the pre-slit injection site 126, it will be understood that as an alternate (FIG. 10), a container 150 could be formed which includes only the pre-slit injection port 126. The removable cover 146 could be used in combination with the container 150.

As illustrated in FIG. 11, the pre-slit injection site 126 can be utilized for the purpose of injecting fluid from the syringe 82, coupled to the shielded cannula 80, into the container 150. When so utilized, the blunt piercing member 98 is used to place the interior fluid containing region 90 of the syringe into fluid flow communication with the interior of the container 150.

FIGS. 12 and 13 illustrate a fluid flow coupling system 151 having as a first element a pre-slit injection site 126a. The site 126a is the same as the site 126 except for a plurality of exterior threads 153 formed on an exterior peripheral surface 155 of the housing 128a. A second element of the coupling system 151 is a shielded blunt cannula 157.

The shielded blunt cannula 157 is sealingly affixed to a flexible tubing member 159 by means of a proximal hollow cylindrical member 161. The member 161 extends into a hollow cylindrical shield 163 to form a blunt piercing member 165.

The shield 163 carries, on an interior peripheral surface, a set of coupling threads 165. The threads 165 match the threads 153.

The two connector elements 126a and 157 slidably engage one another when the shielded cannula 157 moves in an axial direction 167 toward the injection site 126a. The blunt piercing member 165 penetrates the septum 132a.

The coupling member 157 can then be rotated in a direction 169 such the interior set of threads 165 carried thereon engages the exterior set of threads 153. As a result, the two coupling members 126a and 157 are lockingly engaged together with the insertion member 165 extending through the opening 134a in the septum 132a. Hence, fluids can flow from the container 150a via the connector system 126a and 157 through the tubing member 159 to the recipient.

Injection sites of the type described above are also usable in connection with other fluid flow coupling components. For example, with respect to FIG. 14, a pre-slit injection site 160 of the type described above can be used in combination with a spike connector 162 of a conventional variety. Spike connectors such as the spike connector 162 can be used to pierce conventional ports such as the port 106 of the container 104 (FIG. 6). When the spike connector 162 is so used, the pre-slit injection site 160 can then be utilized for the purpose of coupling to other fluid administration sets.

The injection site 160 illustrates an alternate form of swaging the first end 42c for the purpose of retaining the septum 52c therein. The first end 42c can be swaged so as to form an annularly shaped, spiral, spring-like member 164. The member 164 has a free end 164a which engages the exterior dome-shaped peripheral surface 54c of the septum 52c. The spiral, spring-like swaged member 164 will tend to uncoil, thereby continuously applying axial force to the septum 52c and maintaining the domed exterior peripheral surface 54c.

In yet another alternate, FIG. 15 illustrates a pre-slit injection site 166 formed in a Y-junction member 168. The Y-junction member 168 is fixedly attached to first and second tubing members 170 and 172 respectively.

As an alternate to forming the slit 66d completely through the septum 52d, as illustrated in FIG. 16, a slit 66e can be formed only partly through the septum 52e. Such a structure has the further advantage that, until used for the first time, the septum 52e is completely sealed.

The septum 52e can be formed in two parts. One part can have a slit, such as the slit 66e, extending entirely therethrough. A second part can be formed without a slit. These two parts can be located adjacent one another in the first end 42e of the injection site.

The slit 66e may be longer on the top of the septum than the bottom. This feature aids blunt cannula alignment with the slit upon insertion, and aids resealability by minimizing the critical slit sealing interface area.

In accordance with the present invention, the slit could have a length with a range on the order of 0.03 inches (0.0762 centimeters) to 0.150 inches (0.381 centimeters). Preferably, a slit length on the order of 0.07 inches (0.1778 centimeters) will be used in combination with a blunt cannula having a diameter on the order of 0.1 inches (0.254 centimeters).

When initially used, the blunt cannula piercing member, such as the member 98, will be forced through the slit 66a. The lower peripheral surface 56e will then be punctured, providing access for the blunt cannula piercing member 98 into the fluid flow pathway 68e.

Pre-slit injection sites of the type described above can be utilized in combination with burette solution administration sets. One such set 176 is illustrated in FIG. 17. The set 176 includes a pre-slit injection site 178 of the type described above. The injection site 178 is affixed to an exterior planar surface 180 of the burette 182. A removable cover 184 can be used to maintain the injection site 178 in an aseptic condition until blunt cannula 186 or 188 is inserted therethrough.

FIGS. 19 through 23 disclose a method of making a pre-slit injection site in accordance with the present invention. In a first step, a housing 200 is provided. The housing 200 has an interior tapered surface 202 at a first end 202a thereof. The interior peripheral surface terminates in an annular channel 204. A cylindrical septum 206 can be provided adjacent the end 200a.

In a second step, the septum 206 can be forced into the end 202a of the housing 200 and slightly deformed by the tapered peripheral surface 202 using an axially moving die 210. When positioned by the die 210, the septum 206 is located adjacent an internal annular right 212 which bounds the annular channel 204.

In a third step, a second die 214 can be utilized to swage the end 200a into spiral-shaped, spring-like members 200b which apply axially directed forces against an exterior peripheral surface 206a of the septum 206. The axially directed forces form the flat surface 206a into a domed exterior peripheral surface 206b as illustrated in FIG. 23.

Simultaneously, with swaging the end members 200a so as to lock the septum 206 into the housing 200 and to form the domed exterior peripheral surface 206b, a knife 216 can be utilized to form a slit in the septum 206. Alternatively, the slit may be cut by a separate die in a separate step. If the septum 206 is formed as an extrusion, the slit can be created during the extrusion process. If the septum 206 is formed by stamping from a rubber sheet, the slit can be cut during the stamping process. If the septum 206 is formed by compression molding, the slit can be cut during the trimming process.

In order to extrude the slit into rod, a flat pin extrusion bushing can be used. A trailing ribbon may be attached to the bushing. The ribbon would prevent curing material across the slit. The ribbon or wire could be placed in the rod core and later stripped out leaving a slit. An inert substance, such as silicone oil, could be coextruded in the center of the rod to prevent curing across the slit and provide lubrication and a visible target for cannula insertion.

FIGS. 24 and 25 illustrate alternate swaging steps wherein a die 220 moving axially toward the housing 200 swages the end region 200a so as to form an annular U-shaped region 200c and the exterior domed peripheral surface 206c.

The dies 214 or 220 can be formed with various alternate shaped swaging surfaces 224, as illustrated in FIG. 26, depending on the precise shape of the end swage which is desired. It will be understood that all such variations in the swaging operation are within the spirit and scope of the present invention.

The injection site configuration need not be limited to the configurations depicted in FIGS. 3 through 5B, 9, and 12 through 16. Rather, several configurations could be constructed without departing from the scope of this invention. Any such configuration would provide a flexible pre-slit sealing member captured in a chousing which provides compression to create a seal against pressure and a void region to accommodate deformed portions of the sealing member material only when the material is deformed or displaced by a blunt cannula piercing member. One such possible configuration is depicted in FIGS. 27 and 28.

FIGS. 29 and 30 illustrate a tapered cannula structure 250 which is an alternate to the tapered cannula 98. The cannula 250 includes a proximal end 252 with an interior region 254. The region 254 is in part bounded by an internal peripheral wall 256 which is formed with a standard luer taper. The tapered cannula 250 can be formed with a luer-type coupling flange 257 at the proximal end so as to be releasably connectable to the syringe 82 as was the tapered cannula 98 previously discussed.

Extending from the proximal end 252 is a cylindrical tube having a cylindrical mid-region 258 and a distal end member 260. The member 260 has a generally elongated, cylindrical shape with an exterior side wall 262. A centrally located, cylindrical, internal fluid flow path 264 extends through the distal end member 260 and mid-region 258 in fluid flow communication with the interior region 254.

The distal end of the end member 260 has a tapered exterior surface 266. The tapered exterior surface 266 minimizes insertion force as the cannula 250 is being forced through a slit of a septum, such as the slit 66 in the septum 52. The angle of taper of the surface 266 is preferably in a range between 1 to 15 degrees.

The member 260 is also provided with a plurality of elongated grooves 268. The grooves 268 in the exterior wall of the member 260 decrease the surface area of contact at the cannula/septum interface during insertion of the cannula into the injection site 34. This reduced exterior contact surface area decreases the frictional component of the insertion force.

In one embodiment, the tapered blunt cannula 250 may have overall insertion length, corresponding to combined axial lengths of mid-region 258 and end member 260, on the order of 0.375 inches (0.9525 centimeters).

An alternate cannula structure 280 is illustrated in FIGS. 31, 32 and 33. The cannula structure 280 includes a proximal end region 282 corresponding to the end region 252 of the cannula 250. The region 282 includes a luer flange 283. The cannula 280 also includes a central, elongated, cylindrical region 288.

The central region 288 carries at a distal end thereof an elongated cylindrical end member 290. The member 290 includes an exterior, peripheral, cylindrical surface 292 (FIG. 31). The surface 292 is interrupted by a plurality of spaced-apart, elongated slots or apertures 294. The slots 294 are defined by first and second spaced-apart, elongated, parallel side surfaces 294a and 294b. Each of the slots terminates in an end surface 294c at the central region 288.

A fluid flow path 294d extends through the cannula 280. The flow path 294d is in fluid flow communication with the slots 294.

Between the slots 294, at a distal end of the region 290, the exterior surface 292 terminates in tapered end regions 298 to facilitate insertion of the cannula into a pre-slit injection site. The slots 294 themselves also function to decrease the surface contact area, and this further minimizes the insertion force.

The slots 294 are oriented substantially 90 degrees apart around a longitudinal axis 300. The slots 294 increase the internal flow path cross-section. This increases the fluid flow rate.

The slots 294 also provide for enhanced dispersion characteristics owing to the fluid flowing radially out through the slots 294. This radial flow, effecting as change in fluid flow direction of about 90 degrees, promotes flushing and dispersion of fluid through the injection site 34.

Another embodiment of a blunt cannula 310 is illustrated in FIGS. 34 through 37. The cannula 310 is formed with an enlarged proximal connection region 312 corresponding to the region 252 of the cannula 250. The region 312 includes a luer flange 313 and a central fluid flow region 314.

An intermediate, cylindrical region 318 extends from the proximal connection region 312. The cylindrical intermediate region 318 includes a fluid flow path 320 in communication with the fluid flow region 314.

The end region 324 extends from the region 318 and includes a first cylindrical portion 326 into which the fluid flow path 320 extends. The region 326 terminates in a tapered exterior surface 328. The tapered exterior surface 328 merges with a centrally located lead post or guide post 330. The lead post 330 terminates in a hemispherical end surface 332.

The lead post 330 helps locate the septum slit 66 prior to insertion and facilitates penetration of the septum slit 66 by the cannula. The lead post 330 facilitates insertion by providing a very low insertion force at the beginning of the insertion step as the cannula is pushed through the slit, such as the slit 66.

In a preferred embodiment, the guide post 330 can have a length on the order of 0.060 inches (0.1524 centimeters) and a diameter on the order of 0.050 inches (0.127 centimeters).

The end region 318 includes a novel structure for increasing the flow rate and enhancing dispersion characteristics. In particular, the region 318 includes three radially oriented slots 338. Each slot 338 has sides 339a and 339b which each lie along a radius of the cylindrical portion 326 as best illustrated in FIG. 37. The fluid flowing through the cannula 310 undergoes a change in direction (of up to about 90 degrees relative to the cannula center line 337) in the slots 338. This change in direction increases fluid dispersion. Further, since the slots 338 open radially, fluid flow can be maintained even if the end surface 332 of the cannula is pushed up against any material in the system in which the cannula is inserted.

Another embodiment of the tapered cannula of the present invention is illustrated in FIGS. 38 through 40 and is designated generally therein by reference numeral 340. The cannula 340 includes a proximal end 342 which can include a luer coupling flange 344 for cooperating with a suitable mating structure on a syringe. The proximal end 342 also defines an interior region 346.

Extending from the proximal end 342 is a generally cylindrical mid-region 348. Extending from the mid-region 348 is an end member or region 350 which includes a tapered surface 352.

The distal end of the end region 352 terminates in a blunt, arcuate end surface 356. Defined within the mid-region 348 and end region 350 is an internal fluid flow channel 354 which communicates with the interior region 346. Fluid discharges from the flow channel 354 via grooves or apertures 358 in the end region 350. The change in direction of the fluid flow as the fluid passes from the interior channel 354 through the apertures 358 improves fluid dispersion with respect to mixing or flushing in the system downstream of the cannula (e.g., the injection site, drug vial, etc.). The apertures 358 may also function to increase withdrawal force or tug resistance.

Moreover, since the fluid passes radially out through the apertures 358, fluid flow through the cannula 340 can be maintained even when the distal end surface 356 of the cannula is bottomed out or pushed against any material in the system in which the cannula is inserted.

The structure of the cannula 340 is adapted to be constructed with a minimal lead post length (i.e., the portion of the cannula distal end between the end surface 356 and the interior flow channel 354). Further, the design accommodates the use of a minimal tip diameter, minimal taper angle, and minimal cannula diameter. The minimization of these parameters results in a decrease in the peak insertion force required to properly install the cannula in the injection site.

Preferably, the total cross-sectional flow area through the three apertures 358 is about three times the cross-sectional flow area of the interior channel 354. This enhances the flow rate capability compared with a simple open ended cylindrical flow channel of equal length.

The design of the cannula 340 also is effective in reducing or limiting "kick back" or recoil of the cannula after insertion. The resilient material of the septum in an injection site can subject the cannula to forces tending to push the cannula back out of the septum. The kick back forces on the cannula 340 are minimized by the provision of the generally cylindrical mid-region 348.

Another embodiment of the cannula of the present invention is illustrated in FIGS. 41 and 42 wherein the cannula embodiment is designated generally therein by the reference numeral 360. The cannula 360 includes a proximal end 362 defining an interior region 364 and having a luer flange 366 for connection to a suitable mating engaging structure.

A generally cylindrical mid-region 366 extends from the proximal end 362, and an end region 368 extends from the mid-region 366. As with the previous embodiment of the cannula 340 illustrated in FIGS. 38 through 40, the embodiment of the cannula 360 minimizes kick back or recoil owing to the provision of a substantially cylindrical mid-region 366. This design also increases withdrawal or tug resistance.

A generally cylindrical internal flow channel 370 extends through the end region 368 and mid-region 366 in communication with the interior region 364 of the proximal end region 362. The end region 368 is provided with a tapered surface 372. The design permits the use of a very small taper to minimize the insertion force.

Further, the design permits the cannula 360 to be constructed with a small tip diameter, small taper angle, and small cannula diameter so as to reduce the peak insertion force.

Another embodiment of the cannula of the present invention is illustrated in FIGS. 43 through 44 and is designated generally therein by reference numeral 380. The cannula 380 includes a proximal end 382 with a luer flange 384. An interior fluid flow region 386 is defined on the interior of the proximal end 382.

Extending from the proximal end 382 is a mid-region 388. A distal end region 390 extends from the mid-region 388. An internal fluid flow channel or path 392 extends through the end region 390 and mid-region 388, and is in communication with the interior flow region 386.

The end region 390 has an exterior tapered surface 394. This facilitates insertion of the cannula into the injection site. In contrast, the mid-region 388 is generally cylindrical so as to minimize kick back and increase the withdrawal force or tug resistance.

Further, to provide even greater withdrawal force, the mid-region 388 includes an annular barb 396. The barb 396 has a sufficient radius so as to preclude damage to the septum of the injection site and so as to accommodate molding in a straight draw tool. The maximum diameter of the annular barb 396 may typically be on the order of 0.02 inches (0.0508 centimeters) greater than the diameter of the cylindrical mid-region 388. Although the barb 396 functions to prevent inadvertent removal of the cannula 380 from the septum of the injection site, removal of the cannula 380 can still be achieved by entering a sufficiently great axially directed removal force on the cannula 380.

Still another embodiment is illustrated in FIG. 45 which includes a blunt tapered cannula insertion member 400 for insertion into a pre-slit injection site, the cannula 400 having a distal end region 402 with a tapered exterior surface which in the preferred embodiment is an approximately 8 degrees taper. The defined aperture 404 for fluid flow is disposed at the end 406 of the distal end region 402. The end 406 includes a radiused tip defined by a radius of approximately 0.01 inch (0.025 centimeters). The radiused tip reduces insertion force, assists in locating the slit in the injection site and in addition has the practical advantage of facilitating complete filling of the cannula mold cavity.

The tapered surface of the distal end region 402 has an axial length of approximately 0.10 inch in the preferred embodiment. Adjacent to the tapered distal end region is a generally cylindrical region 408 for entering into the injection site behind the distal end region 402, thereby reducing kick back during insertion. The generally cylindrical region 408 has a small draft angle such as about one-half degree.

The force required to insert any of the above-discussed embodiments of the blunt tapered cannula into the septum of the injection site depends upon a number factors: friction at the cannula/septum interface, cannula diameter, cannula taper angle, and degree of septum compression. The cannula/septum interface friction is, in turn, dependent upon lubrication, if any, material properties, and surface finish. It will be understood that the friction at the cannula/septum interface can be reduced by providing a smoother surface finish on the cannula (e.g., by sand blasting the cannula exterior surface) or by molding the cannula so as to produce a matte finish. Conventional lubricants can also be used to further reduce the friction and thereby lower the insertion force required.

In the embodiments of the cannulae described herein, the mid-region and the tapered distal end region may be alternatively characterized as together forming at least one tube defining a fluid flow path therein with the tube having a distal end region for penetrating the injection site.

In preferred contemplated embodiments, the exterior surface of the distal end region may have a taper angle as small as between 1 and 15 degrees.

Further, a locking means, such as the locking arms 100*a* and 100*b* discussed with reference to FIGS. 5A and 5B, may be provided on the cannula embodiments illustrated in FIGS. 29 through 44 to permit the cannulae to be releasably locked to the injection site.

The above described insertion members, usable as part of a blunt cannula, are preferably molded of a plastic formulation including silicone or other lubricant. The use of silicone or other lubricant increases the ease of insertion of that member into the pre-slit injection site.

Figure 46:
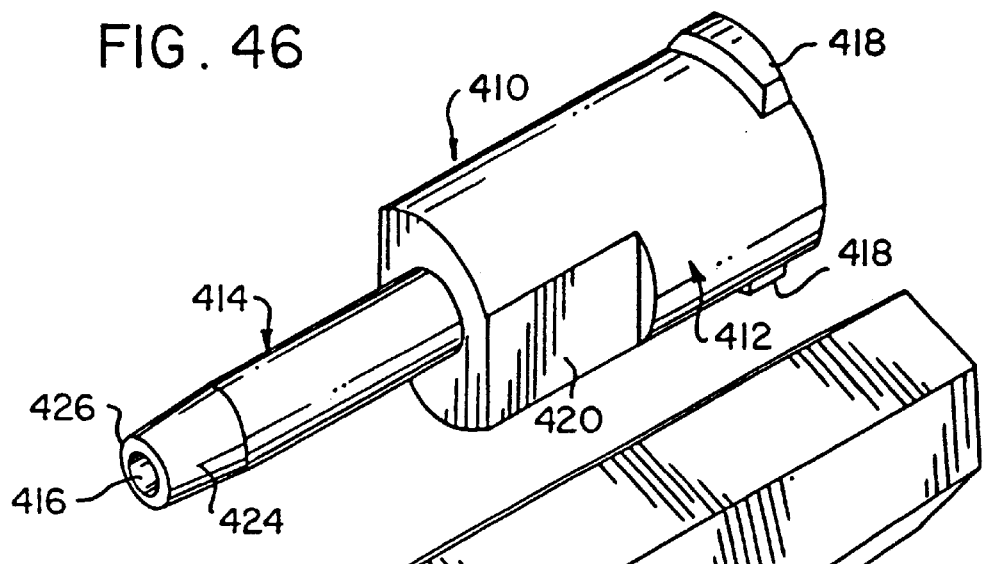
FIG. 46 is a perspective view of another embodiment of a blunt cannula embodying the present invention.

FIG. 46 shows a blunt cannula member, generally at 410, for use with the pre-slit injection sites disclosed herein. The blunt cannula member 410 generally has a hollow cylindrical portion 412 and a blunt cannula portion 414. The blunt cannula member 410 is preferably of one-piece molded, rigid plastic, with a through bore 416 extending through the blunt cannula portion and communicating with the hollow cylindrical portion.

The hollow cylindrical portion has a pair of opposed raised flanges or threads 418 for threaded engagement with other devices, for example, syringes, administration sets and the like. Internally, the hollow cylindrical portion 412 may also be adapted for attachment to other devices. For example, the internal surface of the cylindrical portion may define a tapered female luer surface for interfitting with the standard male luer connectors utilized in many medical devices, as is well known in the medical field. The hollow cylindrical portion 412 may also include a pair of opposed flat surfaces 420 for cooperation with a tip protector or shield such as depicted in FIG. 47, which is described below.

The blunt cannula portion 414 extends generally axially from the hollow cylindrical portion 410. The cannula portion is generally cylindrical throughout the greater part of its length, with a tapered end portion 424, which narrows to the blunt end edge 426.

Figure 47:
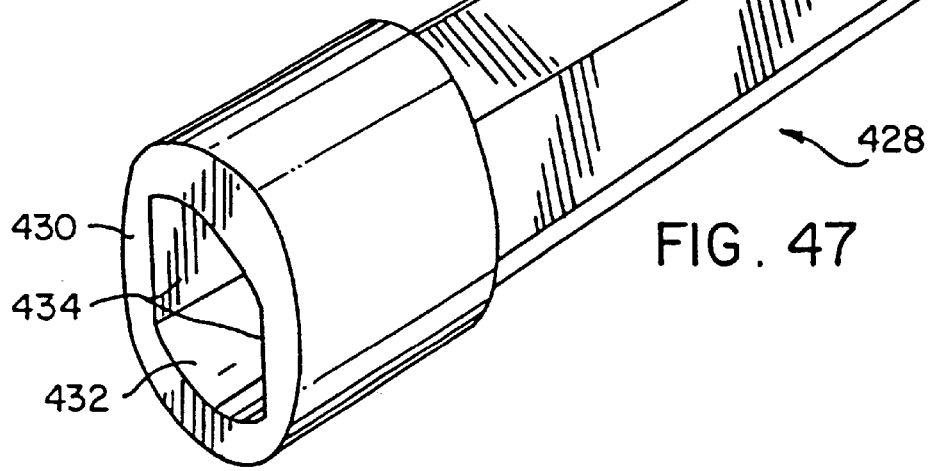
FIG. 47 is a perspective view of a blunt cannula shield or tip protector.

FIG. 47 is an enlarged view of a hollow shield or tip protector 428 for covering and protecting a blunt cannula, such as, for example, the blunt cannula portion 414 of blunt cannula member 410 shown at FIG. 46 or other blunt cannulae as disclosed herein. The shield 428 has a generally elongated housing 430, which is open at one end for receiving the blunt cannula. At the open end, the interior surface 432 of the shield generally corresponds to the shape of the exterior surface of the blunt cannula portion 412, i.e., it is generally cylindrical, with a pair of opposed flat surfaces 434 matching the flat surfaces 420 of the blunt cannula device 410. Further, either surfaces 432 or 434 can be provided with standing ribs to control the depth of insertion of the blunt cannula portion 414 into housing 430. The matching flat surfaces of the shield and the blunt cannula device allow a user to secure the blunt cannula onto a syringe or similar device, for example, without exposing the cannula portion 414 to touch contamination. When access to the blunt cannula is required, the shield may simply be slidably removed from the cannula. As can be appreciated, the outer surface of the shield 428 can be shaped in such a manner or provided with a roughened finish to assist the user in gripping or removing shield 428 from the cannula.

Typically, the blunt cannula 410 or other blunt cannula device and shield 428 would be provided in a joined sterile configuration. The shield 428 can be provided with channels to facilitate gas sterilization. The user preferably leaves the shield on to prevent inadvertent contamination when attaching the blunt cannula to the mating product, e.g., the male luer fitting of a syringe or administration set. The matching flat surfaces 432 of the shield and 420 of the blunt cannula act as a wrench to allow any twisting force applied to the shield to be transmitted to the cannula, e.g., for threading the cannula onto a luer lock device or for applying a twisting force in making a luer slip connection.

Figure 48:
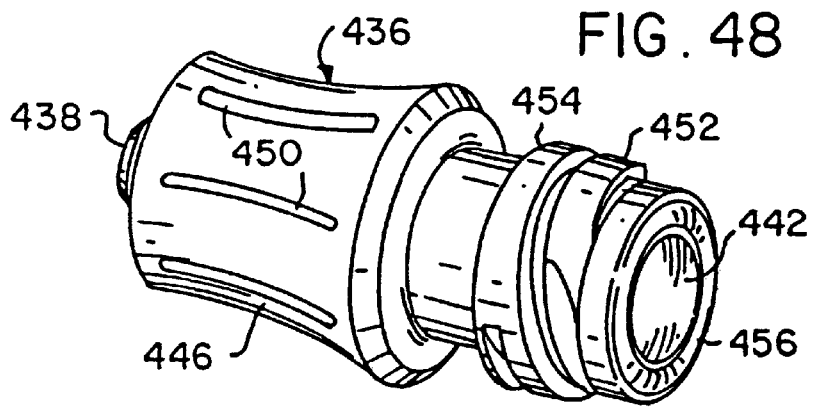
FIG. 48 is a perspective view of a heparin lock embodying the present invention.

FIG. 48 shows what is commonly referred to as a heparin lock, generally at 436, employing a pre-slit injection site 442 and other features of the present invention. The heparin lock 436 may be attached, for example, to the end of a venous catheter.

During intravenous therapy, it is not unusual for the administration of liquid to be interrupted from time to time. Instead of performing a new catheterization procedure each time administration is to be restarted, it is often preferable to utilize the same catheter, thus reducing the number of catheterization procedures, more colloquially referred to as the number of "sticks," and reducing the trauma and risk associated with each such procedure.

To maintain the patency of the catheter during interruption, and prevent blood from clotting and clogging the catheter, it is a common practice to attach an injection site over the catheter and fill the catheter with heparin or other anticoagulant. The heparin lock 436 shown in FIG. 48 is for attaching to a patient's catheter for maintaining patency of the catheter during interruption in fluid flow.

Figure 49:
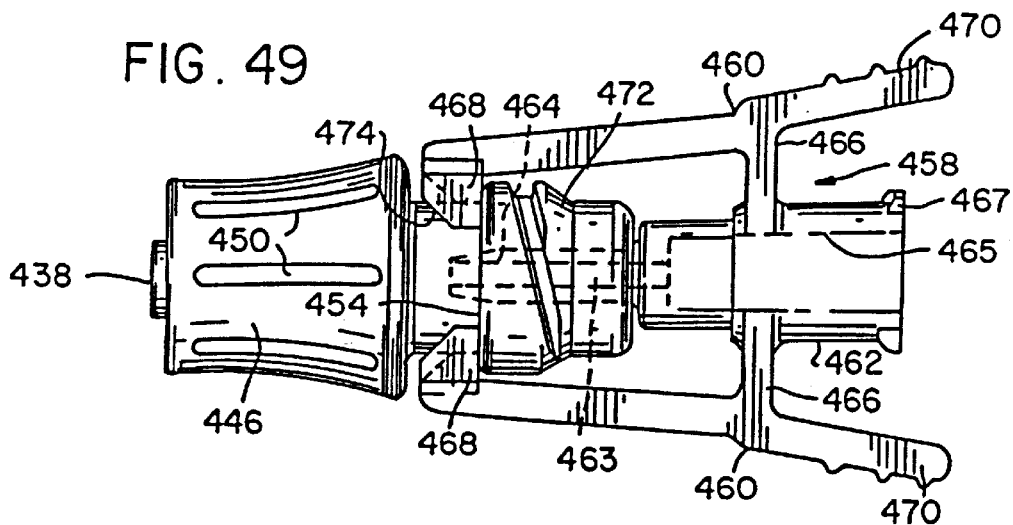
FIG. 49 is a side elevational view of the heparin lock of FIG. 48 in joined relationship with a blunt cannula device of alternative construction embodying the present invention.
Figure 50:
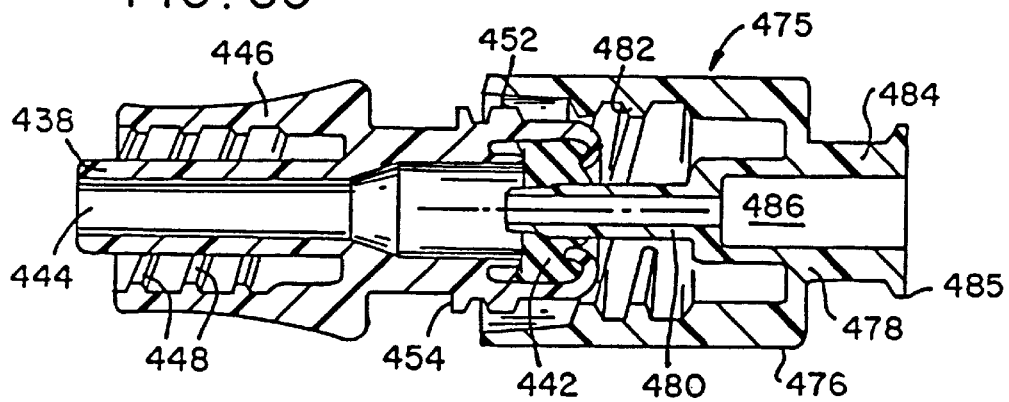
FIG. 50 is a cross-sectional view of the heparin lock of FIG. 48 in joined relationship with a blunt cannula device of further alternative construction embodying the present invention.

The heparin lock 436, also shown in FIGS. 49 and 50, has a first end portion 438 in the form of a male luer connector for sealingly engaging a complementary female tapered luer surface on the patient's catheter (see cross-sectional view in FIG. 50). The other end of the heparin lock 436 includes a pre-slit injection site 442 of the type previously discussed in detail. An axial fluid flow passageway 444 communicates between the pre-slit injection site and the end of the male luer for fluid flow therebetween.

The tapered exterior surface of the male luer 438 is substantially surrounded by generally cylindrical gripping collar 446. Threads 448 are provided on the interior surface of the collar for threadedly engaging a standard luer lock connector, as is often found on intravenous catheter devices. The exterior surface of the collar 446 is generally arcuate in cross-sectional shape (as best seen in FIGS. 49 and 50), to provide a gripping surface. The surface curves generally outwardly in a direction toward the pre-slit injection site 442. This allows the nurse, physician or attending staff member to grip the heparin lock and to reduce any force exerted during entry of a blunt cannula into the pre-slit injection site from being transmitted to the venous catheter. For improvement in the gripping, a series of axial grooves 450 are provided in the exterior surface of the collar 446.

In accordance with other aspects of the present invention, the heparin lock includes features which allow attachment to various styles or types of blunt cannulae. For example, as best seen in FIG. 48, threads 452 are provided on the exterior surface of the cannula for threaded locking engagement to a blunt cannula device of the type having an interiorly threaded sleeve or shield, such as depicted in FIG. 50. The heparin lock 436 also includes a generally radially-extending shoulder 454 for locking retention of resilient gripping fingers on a blunt cannula device of the type shown in FIG. 49.

As a safety measure, and to prevent staff confusion of an injection site of the present invention with other injection sites which are for use with needles, a visual identifier is also provided with the heparin lock of FIG. 48. Such an identifier may also be provided with the other pre-slit injection site devices described above. The identifier may take the form of any unique color or configuration which allows the staff member to determine that the heparin lock 436 embodies the present invention and is intended for use with blunt cannulae. In the preferred embodiment, however, the visual identifier comprises a distinct color identifier and, more particularly, is a brightly colored ring 456 (FIG. 48) circumscribing the pre-slit injection site 442. While the color selected may vary depending on application, it should be a color which is distinct from and in contrast to the color of any plastic used in the manufacture of the heparin lock.

As noted earlier, the heparin lock 436 depicted in FIG. 48 may be used with a variety of styles or types of blunt end cannula devices. For example, the heparin lock may be used with a bare blunt end cannula, such as that depicted in FIG. 46, which does not lock onto to the heparin lock. Alternatively, as shown in FIG. 49, the heparin lock may be used in combination with a blunt cannula device 458 which utilizes a pair of resilient gripping fingers 460 for retaining the blunt cannula in joined relationship with the heparin lock. The blunt cannula device 458 depicted in FIG. 49 has a generally cylindrical, hollow base or body portion 462 and a blunt cannula portion 464 substantially as described earlier in connection with FIG. 46 or with the other figures of the present inventions. A fluid flow path 463 extends through the blunt cannula portion and communicates with a female luer connection 465 defined in the hollow body portion for fluid flow through the blunt cannula device. Flanges or threads 467 on the body portion permit the attachment of a male luer lock connector to the blunt cannula device.

Each of the gripping fingers 460 is mounted to the body portion of the blunt cannula device by an intermediate radially extending wall portion 466. The gripping fingers have radially inwardly directed retention means 468 at one end for engaging against radial shoulder 454, and gripping means 470 at the other end for squeezing and spreading the retention means to release the blunt cannula device from the heparin lock. In the as-molded condition, the gripping fingers are biased radially inwardly, toward the blunt cannula portion 464. Because of the natural resilience of the plastic, the retention end of the fingers may be spread by squeezing the gripping end of the fingers. The natural resilience will hold the retention means in the lock position (shown in FIG. 49) until manually released.

When used in combination with a heparin lock such as depicted in FIG. 48, the blunt cannula device 458 may be attached by simply pushing the blunt cannula into the pre-slit injection site 442. A forward facing tapered surface 472 (FIG. 49) in front of the threads engages a similar tapered surface 474 on the retention means 468 so as to naturally spread the fingers 460 apart as the blunt cannula is forced into the pre-slit injection site. After the blunt cannula is inserted into pre-slit injection site sufficiently far so that the retention means are beyond the radial shoulder 454, the gripping fingers will snap inwardly behind the shoulder, holding the blunt cannula in the position depicted in FIG. 49.

To withdraw the blunt cannula, the user need simply squeeze the gripping end 470 of the handles, which will spread the retention means of the fingers and release the blunt cannula device from the heparin lock.

The heparin lock of FIG. 48 is also useful with a blunt cannula device 475 having an internally threaded shield or sleeve, such as depicted in FIG. 50. FIG. 50 illustrates the blunt cannula device 475 as it first enters the pre-slit injection site 442 of the heparin lock and prior to engagement with the heparin lock threads 452. The blunt cannula device shown in FIG. 50 has a generally cylindrical outer wall 476 and a transverse end wall 478. A blunt cannula 480 extends through the end wall. The blunt cannula may be constructed in generally the same manner as the blunt cannula portion depicted in FIG. 46 or in accordance with the other embodiments of the present invention.

The cylindrical outer wall 476 preferably extends beyond the tip end of the blunt cannula to protect the cannula against inadvertent touch contamination. The interior surface of the cylindrical wall is preferably threaded at 482 for threadedly engaging the device to which the blunt cannula is attached, such as the heparin lock depicted in FIG. 48. As noted above, FIG. 50 depicts the blunt cannula device 475 at an initial entry position. Further insertion of the blunt cannula and simultaneous turning of the blunt cannula device results in threaded locking engagement between the blunt cannula device 475 and the heparin lock.

The blunt cannula 480 of the blunt cannula device 475 is in fluid communication with an entry port, generally defined by wall 484, which extends in the opposite direction of the blunt cannula, from the other side of the transverse wall. The entry port is for attachment to other devices such as syringes, tubing, administration sets or the like, and may take such form as is appropriate for the particular device to which it is attached. The entry port 484 preferably has a tapered inner surface for receiving a standard male luer fitting of a syringe or the like, and may include external threads or flanges 485 for attachment to a luer lock. Another embodiment provides the entry port 484 as having a tapered inner surface for receiving a tubing fit. A fluid passageway 486 extends continuously through the entry port and the cannula portion for flow therebetween.

Figure 51:
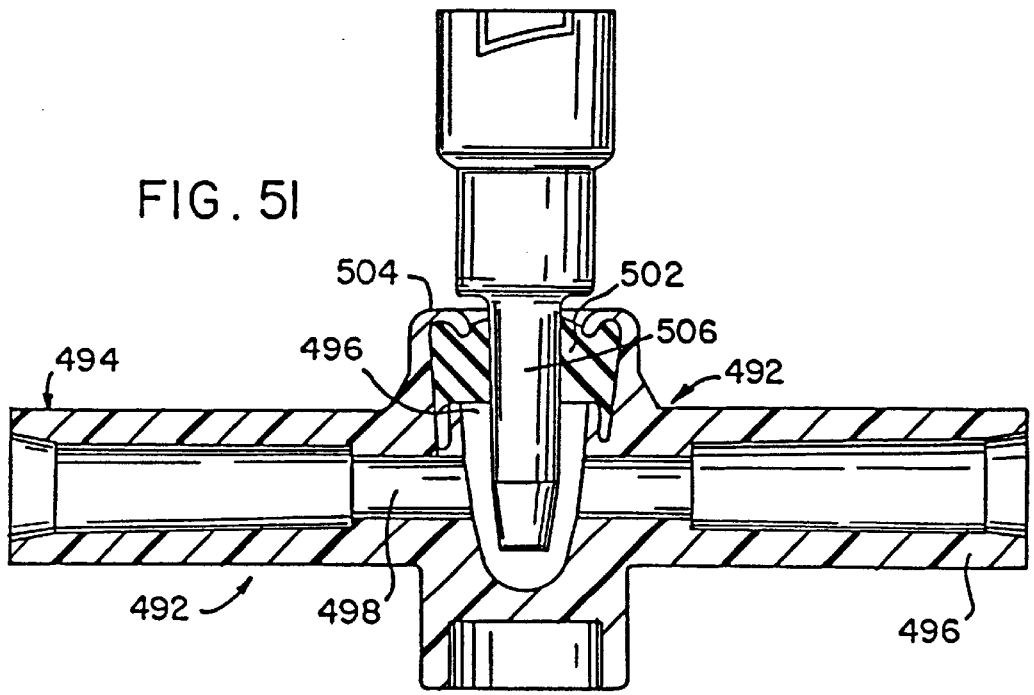
FIG. 51 is a cross-sectional view of a pre-slit in-line injection site embodying the present invention in joined relationship with a blunt cannula shown in side elevational view.

FIG. 51 shows, in cross-sectional view, a further alternative device 492 which may employ the pre-slit injection site of the present invention. The pre-slit injection site device 492 depicted in FIG. 51 is an in-line device, preferably for adding medication to a fluid stream, removing a sample from a fluid stream, or similar application. The device depicted in FIG. 51 has a fluid entry port 494 at one end, a fluid exit port 496 at the other end, and a fluid passageway 498 communicating directly between the entry and exit ports. The inlet and outlet may have such additional features as are useful connecting the injection site device within a fluid flow path. As depicted, the inlet defines a slightly tapered female surface and the outlet defines a similarly female tapered surface which are preferably joined by solvent bonding a similar attachment to plastic tubing of an administration set, extension set or the like. Standard luer fittings or surfaces could also be provided at the inlet or outlet, as desired.

For injecting liquid into the fluid stream or sampling the fluid stream, the device has a side channel 496 which communicates between a pre-slit septum 502 made and assembled in accordance with the present invention, and the fluid passageway 498. The septum 502 is made as described above, and mounted and held in position by a swaged-over wall 504, as previously described, which may include a colored identifier ring around the septum.

In accordance with the present invention, a blunt cannula, such as cannula 506, may be inserted through the pre-slit septum for injecting fluid into the liquid stream flowing between the inlet and outlet, or for taking samples of the fluid stream.

The in-line injection site device 492 shown in FIG. 51 may be used in combination with a bare blunt cannula, such as that depicted in FIG. 51, or may be used in combination with the blunt cannula device 458, depicted in FIG. 49, when a locking relationship between the blunt cannula and injection site is desired.

Figure 52:
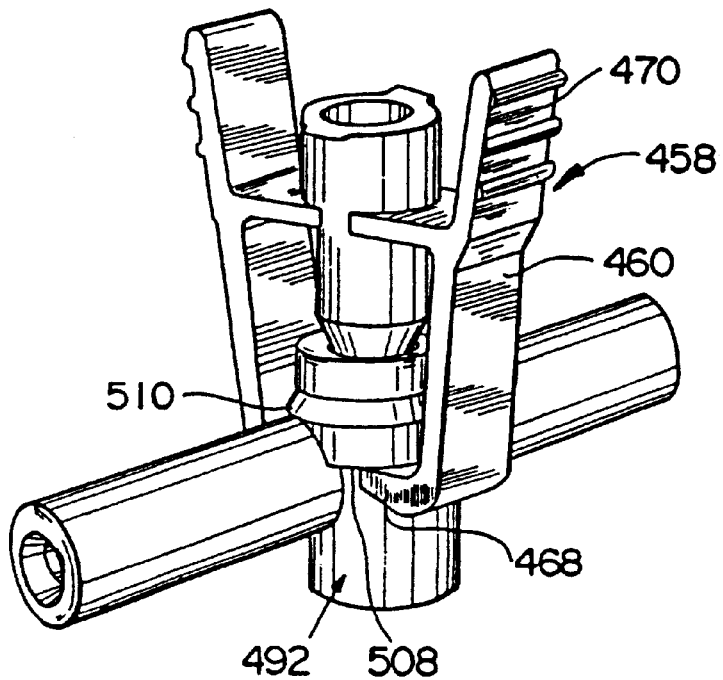
FIG. 52 is a perspective view of the alternative blunt cannula device of FIG. 49 in joined and locked relationship with the pre-slit in-line injection site depicted in FIG. 51.

As depicted, for example, in FIG. 52, the blunt cannula device 458 may be attached in a secure locking relationship to the in-line injection site 492. As shown there, the in-line injection site has a radially extending shoulder 508 on each side of the housing, for engaging against the retention means 468 on the end of the resilient gripping fingers 460. As with the heparin lock, the in-line injection site also includes a generally tapered surface 510 defined on the exterior surface for spreading the retention means as the blunt cannula is inserted into the injection site. As was described above, insertion of the blunt cannula into the injection site results in the retention means being spread by the tapered surface 510 and, as the blunt cannula is inserted farther, the retention means snap into a locking position behind the radial shoulder 508. In this arrangement, the blunt cannula is securely locked onto the injection site and inadvertent withdrawal is thus prevented. To remove the blunt cannula from the in-line injection site, the gripping ends 470 of the resilient fingers are squeezed, causing spreading of the retention means 468 and release from the injection site. The cannula may then be simply removed by withdrawing it from the injection site.

Figure 53:
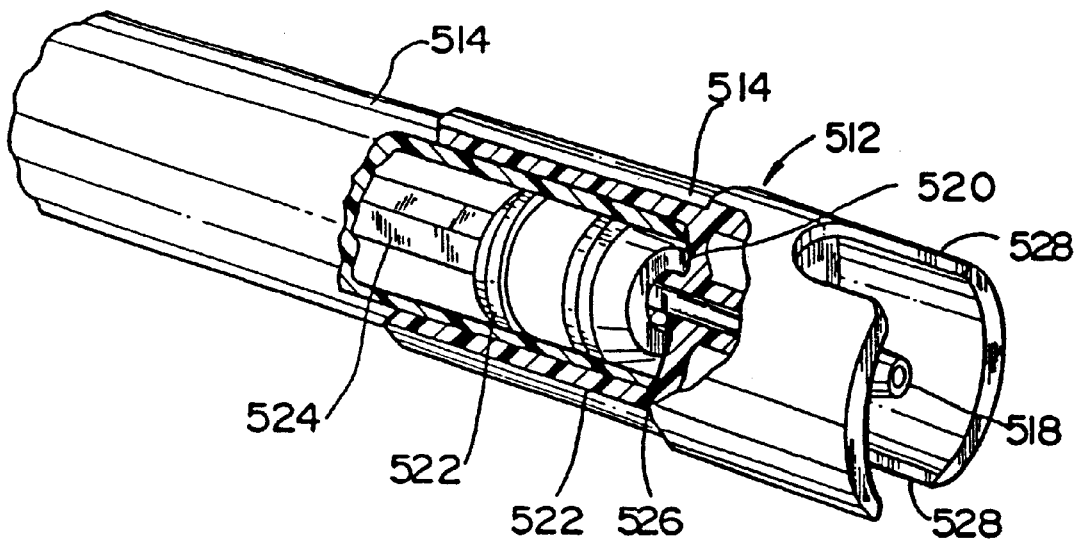
FIG. 53 is a perspective view, partially broken away, depicting the combination of a syringe and an alternative blunt cannula device of the present invention for injecting or removing liquid through a pre-slit in-line injection site, such as depicted in FIG. 51.

FIG. 53 depicts yet a further embodiment of the present invention. That figure depicts a blunt cannula device 512 embodying the present invention in combination with a syringe 514. The blunt cannula device 512 has a generally cylindrical outer wall 516 which encloses and substantially protects a blunt cannula portion 518. The blunt cannula portion is attached to and extends from an intermediate transverse interior wall 520. The blunt cannula device 512 may be attached to a syringe in various ways. As depicted, however, the syringe 514 has a glass barrel wall which is tightly press fit into one end of the cylindrical outer wall, extending therewithin to the transverse wall 520.

Although various syringes may be used in connection with the blunt cannula device 512 without departing from the present invention, the syringe depicted in FIG. 53 is of the type prefilled with a medical liquid such as heparin. Although it does not form a part of the present invention, for purposes of completeness, the syringe depicted in FIG. 53 has a pair of resilient pistons 522 spaced apart, with the fluid to be dispensed contained between the pistons. A plunger rod 524 pushes the pistons forward until the forward most piston engages against an entry port 526 which extends in a direction opposite the blunt cannula 518. The forwardmost piston has a frangible portion, which is pierced by the entry port, releasing the liquid contained between the pistons for expulsion through the blunt cannula.

In accordance with the present invention, the blunt cannula portion 518 is substantially protected from inadvertent touch contamination by the outer cylindrical wall 516. To permit the blunt cannula to be used, however, with the in-line injection site 492 or a similar device, a pair of opposed, generally U-shaped recesses 528 are provided in the cylindrical wall for receiving the inlet and outlet portions 494, 496 of the in-line injection site when the cannula is attached to it. This arrangement is depicted in a perspective view in FIG. 56. As shown there, the blunt cannula device 512 may be attached to the in-line injection site by inserting the blunt cannula portion into the pre-slit injection site, with the U-shaped recesses 528 receive the inlet and outlet portions 494, 496 of the in-line injection site, thus allowing the bare cannula to be inserted sufficiently far into the pre-slit injection site.

Figure 54:
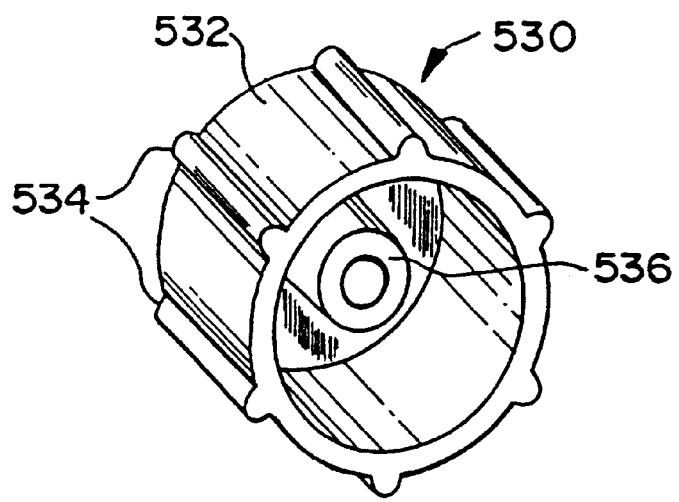
FIG. 54 is a perspective view of a blunt cannula shield or tip protector for attachment over the end of the blunt cannula device such as depicted in FIG. 53.

FIG. 54 shows a shield or tip protector 530 for a blunt cannula device of the type shown in FIG. 53. The tip protector 530 has a generally cylindrical outer wall 532 with raised ribs 534 for gripping. The cylindrical wall is sized to slip over the end cylindrical wall 514 of the blunt cannula device 512, and is sufficiently long to extend beyond the U-shaped recesses to completely enclose and protect the blunt cannula 518 during shipping, storing and between uses, if so desired.

Concentrically disposed within the cylindrical wall 532, the tip protector has an axially extending, hollow tube 536 for slidably receiving the blunt cannula 518 therewithin. The shield or tip protector 530 would typically be attached to the blunt cannula device 512 during manufacture, and removed when the syringe and blunt cannula device are used. If so desired, it may be reattached between uses to protect the cannula from any further contamination.

Figure 55:
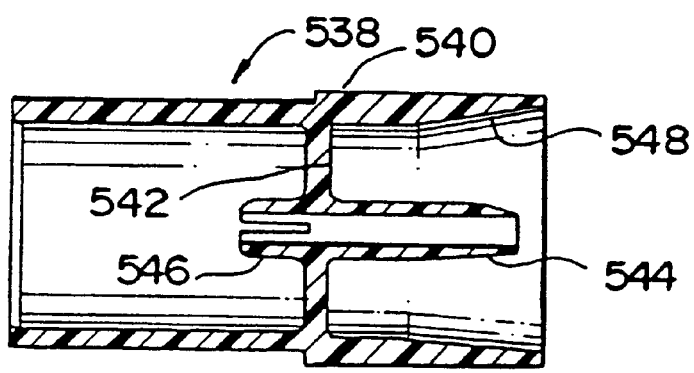
FIG. 55 is a cross-sectional view of an alternative blunt cannula device particularly suited for attachment to a syringe as shown in FIG. 53.
Figure 56:
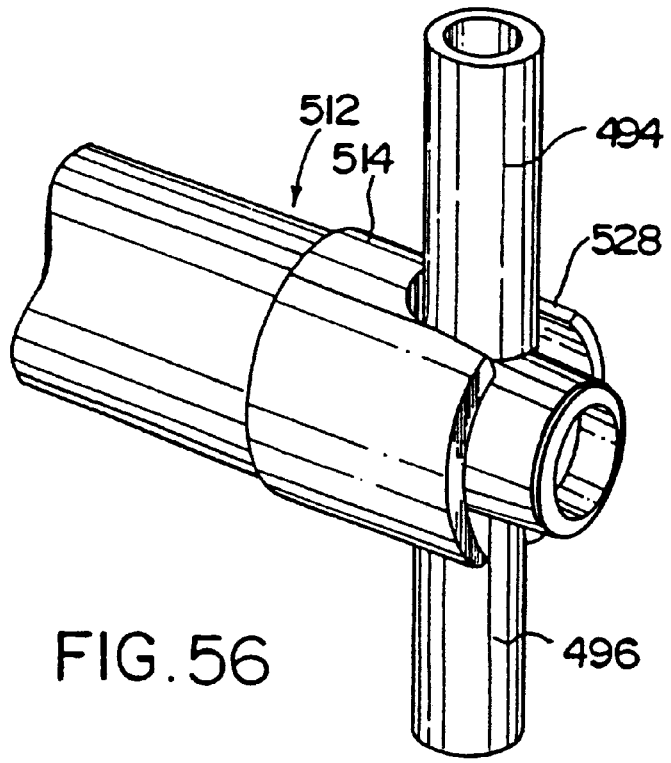
FIG. 56 is a perspective view of the blunt cannula device shown in FIG. 53 in joined relationship with the pre-slit injection site shown in FIG. 51.

FIG. 55 is an alternative embodiment of the blunt cannula device shown in FIG. 53, and is depicted without a syringe attached to it. As shown in FIG. 55, the blunt cannula device 538 similarly has a cylindrical outer wall 540, a transverse intermediate inner wall 542, a blunt cannula 544 extending axially from the transverse intermediate wall and an entry port 546 extending in the opposite direction from the blunt cannula. The essential difference between this embodiment and the one shown in FIG. 53 is the absence of U-shaped recesses for use with an in-line injection site such as depicted in FIG. 56. For ease of attachment to an injection site, the inner surface of the cylindrical wall is preferably tapered at 548.

From the foregoing, it will be observed that numerous variations and modifications may be effected without departing from the spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. An in-line site a fluid stream and usable with a blunt cannula device, the site comprising:
   a housing defining an inlet and an outlet and a fluid flow path channel therethrough and a side channel which communicates with said fluid flow path channel;
   tubing members connected to said inlet and said outlet;
   a housing and resilient sealing means forming a seal for an end of said side channel, said housing including a first end defining a tapered interior surface and terminating in an annular member, wherein said tapered interior surface terminates in an annular channel formed by a ridge projecting inwardly from said interior surface, and said resilient sealing means being carried by said housing and including a generally cylindrical sealing member having a first end and a second end and being positioned in said housing first end adjacent said tapered interior surface such that a void is created by said annular channel, said sealing member having a resealable opening therein and being axially compressed around a peripheral edge of its first end by said annular member, wherein said opening opens outwardly such that a blunt cannula can be sealingly inserted through said opening and placed in fluid flow communication with said flow channel and such that the blunt cannula can be removed therefrom with said flexible means interacting with said housing so as to reseal said resealable opening, said tapered interior surface interacting with a side peripheral surface of said sealing member so as to generate resealing radial forces, directed inwardly toward a centerline in said flow channel, to urge said resealable opening into a closed condition, and so as to deform said sealing member side peripheral surface to conform to said tapered interior surface, and wherein said flexible means contacts said ridge during insertion of the blunt cannula through said resealable opening and deforms into said annular channel; and
   said first end including means, engaged with said peripheral surface, for retaining said sealing means therein.

2. The in-line injection site of claim 1 wherein prior to insertion of the blunt cannula, said resealable opening only extends part way through said sealing means.

3. The in-line injection site of claim 1 wherein said resealable opening extends entirely through said sealing means.

4. The in-line injection site of claim 1 wherein said radial resealing forces increase through said flow channel from a minimum at said dome-shaped surface.

5. The in-line injection site of claim 1 wherein a first tubing member and a second tubing member are attached to the housing.

6. The in-line injection site of claim 1 wherein the sealing member has a dome-shaped outwardly facing surface.

7. The in-line injection site of claim 1 including a locking means on said housing that cooperates with a locking means of the blunt cannula.

8. The in-line injection site of claim 7 wherein the locking means of the blunt cannula includes a pair of gripping fingers.

9. The in-line site of claim 1 wherein the site is configured as a y-site.

10. An in-line injection site usable with a blunt cannula comprising:
    a housing having a first end defining an inlet to a fluid flow path, at least one channel that defines a second fluid flow path that is not parallel to the fluid flow path, said first end bounded in part by an annular lip, wherein an interior surface of the housing has a narrowing taper that terminates in an annular channel formed by a ridge projecting inwardly from the interior surface;
    cylindrical resilient sealing means positioned on a selected surface of said lip, said sealing means defining a resealable cannula receiving opening therethrough, said sealing means having an exterior peripheral surface around said resealable opening and being positioned against said interior surface such that a void is created by said annular channel; and
    means for retaining said sealing means adjacent said lip including force-applying means for urging said resealable opening to a sealed condition, said force-applying means including an annular retaining collar, carried by said first end, for engaging said exterior peripheral surface of said sealing means to apply axially directed forces to said sealing means so as to axially compress said sealing means around said exterior peripheral surface, wherein said resealable opening opens outwardly such that a blunt cannula can be sealingly inserted through said opening and placed in fluid flow communication with said fluid flow path and such that the blunt cannula can be removed therefrom with said flexible means interacting with said housing interior surface so as to reseal said resealable opening, and wherein said sealing means contacts said ridge during insertion of the blunt cannula through said resealable opening and deforms into said annular channel.

11. The in-line injection site as in claim 10, with said sealing means including a cylindrically shaped flexible member.

12. The in-line injection site of claim 10 with said retaining collar formed as a generally U-shaped member.

13. The in-line injection site of claim 10 wherein said resealable opening extends entirely through said sealing means.

14. The in-line injection site of claim 10 including a first tubing member attached to the housing and a second tubing member are attached to the housing.

15. The in-line injection site of claim 10 wherein the sealing means has a dome-shaped outwardly facing surface.

16. The in-line injection site of claim 10 including a locking means on said housing that cooperates with a locking means of the blunt cannula.

17. The in-line injection site of claim 16 wherein the locking means of the housing of the blunt cannula is a pair of gripping fingers.

18. The in-line injection site of claim 10 wherein the housing defines a y-site.

19. An in-line site usable with a blunt cannula comprising:

a housing defining an in-line site and comprising a first end and a first fluid flow path and a second fluid flow path, said first end bounded in part by an annular lip, wherein an interior surface of the housing has a narrowing taper that terminates in an annular channel formed by a ridge projecting inwardly from the interior surface;

cylindrical resilient sealing means positioned on a selected surface of said lip, said sealing means including a cylindrical shaped flexible member having first and second spaced apart surfaces and defining a resealable cannula receiving opening therethrough, and said sealing means having an exterior peripheral surface around said first surface and being positioned against said interior surface such that a void is created by said annular channel, said resealable opening at said first surface; and means for retaining said sealing means adjacent said lip including force-applying means for urging said resealable opening to a sealed condition, said force-applying means including an annular retaining collar formed as a generally U-shaped member carried by said first end, for engaging said exterior peripheral surface of said sealing means to apply axially directed forces to and deforming said sealing, wherein said resealable opening opens outwardly such that a blunt cannula can be sealingly inserted through said opening and placed in fluid flow communication with said flow path and such that the blunt cannula can be removed therefrom with said flexible means interacting with said housing interior surface so as to reseat said resealable opening, and wherein said sealing means contacts said ridge during insertion of the blunt cannula through said resealable opening and deforms into said annular channel.

20. The in-line site of claim 18 wherein a first tubing member and a second tubing member are/attached to the housing.

21. The in-line site of claim 18 wherein the sealing means has a dome-shaped outwardly facing surface.

22. The in-line site of claim 18 including a locking means on said housing that cooperates with a locking means of the blunt cannula.

23. The in-line site of claim 21 wherein the locking means of the blunt cannula is a pair of gripping fingers.

24. The in-line site of claim 20 wherein the site has a y-site shape.

* * * * *